(12) United States Patent
Ayyala

(10) Patent No.: US 8,337,447 B2
(45) Date of Patent: Dec. 25, 2012

(54) DEVICE FOR DELIVERY OF ANTIFIBROTIC AGENTS AND METHOD

(76) Inventor: Ramesh S. Ayyala, New Orleans, LA (US)

( * ) Notice: Subject to any disclaimer, the term of this patent is extended or adjusted under 35 U.S.C. 154(b) by 411 days.

(21) Appl. No.: 12/277,139

(22) Filed: Nov. 24, 2008

(65) Prior Publication Data

US 2009/0124955 A1 May 14, 2009

Related U.S. Application Data

(63) Continuation-in-part of application No. PCT/US2007/012253, filed on May 23, 2007.

(60) Provisional application No. 60/808,446, filed on May 25, 2006.

(51) Int. Cl.
*A61M 5/00* (2006.01)

(52) U.S. Cl. .................................. 604/9; 604/8

(58) Field of Classification Search .................. 604/8, 9; 623/6.16
See application file for complete search history.

(56) References Cited

U.S. PATENT DOCUMENTS

| | | | | |
|---|---|---|---|---|
| 6,102,045 | A * | 8/2000 | Nordquist et al. | 128/898 |
| 6,201,001 | B1 * | 3/2001 | Wang et al. | 514/396 |
| 6,464,724 | B1 | 10/2002 | Lynch et al. | |
| 6,666,841 | B2 * | 12/2003 | Gharib et al. | 604/8 |
| 6,939,375 | B2 | 9/2005 | Sirhan et al. | |
| 2002/0143284 | A1 * | 10/2002 | Tu et al. | 604/9 |
| 2003/0149479 | A1 * | 8/2003 | Snyder et al. | 623/6.16 |
| 2004/0096477 | A1 * | 5/2004 | Chauhan et al. | 424/429 |
| 2005/0119737 | A1 * | 6/2005 | Bene et al. | 623/4.1 |
| 2005/0182463 | A1 * | 8/2005 | Hunter et al. | 607/115 |
| 2005/0277864 | A1 * | 12/2005 | Haffner et al. | 604/8 |
| 2005/0281883 | A1 | 12/2005 | Daniloff et al. | |
| 2005/0283108 | A1 | 12/2005 | Savage | |
| 2006/0195187 | A1 * | 8/2006 | Stegmann et al. | 623/4.1 |
| 2007/0156079 | A1 * | 7/2007 | Brown | 604/9 |

OTHER PUBLICATIONS

Written Opinion of International Search Authority, PCT/US2007/12253, Nov. 21, 2007.
Communication for Which No Other Form Is Applicable, International Search Report, PCT/US2007/12253, Jan. 30, 2008.
Chian-Huey Hong et al, Glaucoma Drainage Devices: A Systematic Literature Review and Current Controversies, 2005.
Ayyala et al, Comparison of Different Biomaterials for Glaucoma Drainage Devices, Feb. 1999.
Ayyala et al, Comparison of Different Biomaterials for Glaucoma Drainage Devices Part 2, Aug. 2000.
Hinkle, A Comparison of the Polypropylene Plate, Ahmed Glaucoma Valve to the Silicone Plate, Ahmed Glaucoma Flexible Valve, Apr. 23, 2007.
Kyoko Ishida et al, Comparison of Polyrpopylene and Silicone Ahmed Glaucoma Valves, American Academy of Ophthomology 2006.
Blake et al, Inhibition of Cell Profilereation by Mitomycin C Incorporated Into P(HEMA) Hydrogels, J. Glaucoma, vol. 5, No. 4, Aug. 2006.
Chen et al, Use of Antifibrosis Agents and Glaucoma Drainage Devices in the American and Japanese Glaucoma Societies, Journal of Glaucoma, 1997.

(Continued)

*Primary Examiner* — Leslie Deak
(74) *Attorney, Agent, or Firm* — John J. Connors; Connors & Assoc. pc

(57) ABSTRACT

An ophthalmological device comprises an implant member carrying an antifibrotic agent that is released slowly over a prolonged period when inserted into a wound in an eye produced by surgery. The member is placed in the vicinity of a wound created during the surgery to inhibit inflammatory cell proliferation, thereby preventing the growth of fibrous tissue after the eye surgery.

25 Claims, 17 Drawing Sheets

OTHER PUBLICATIONS

Joshi et al, Survey of the American Glaucoma Society, 2005.

Broadway, et al, Local Effects of Previous Conjunctival Incisional Surgery and the Subsequent Outcome of Filtration Surgery, Elsevier Science Inc, 1998.

Ayyala et al, A Clinical Study of the Ahmed Glaucoma Valve Implant in Advanced Glaucoma, Oct. 27, 1997.

Cantor et al, The Effect of Mitomycin C on Molteno Implant Syrgery, A 1-Year Randomized, Masked, Prospective Study, Oct. 27, 1997.

* cited by examiner

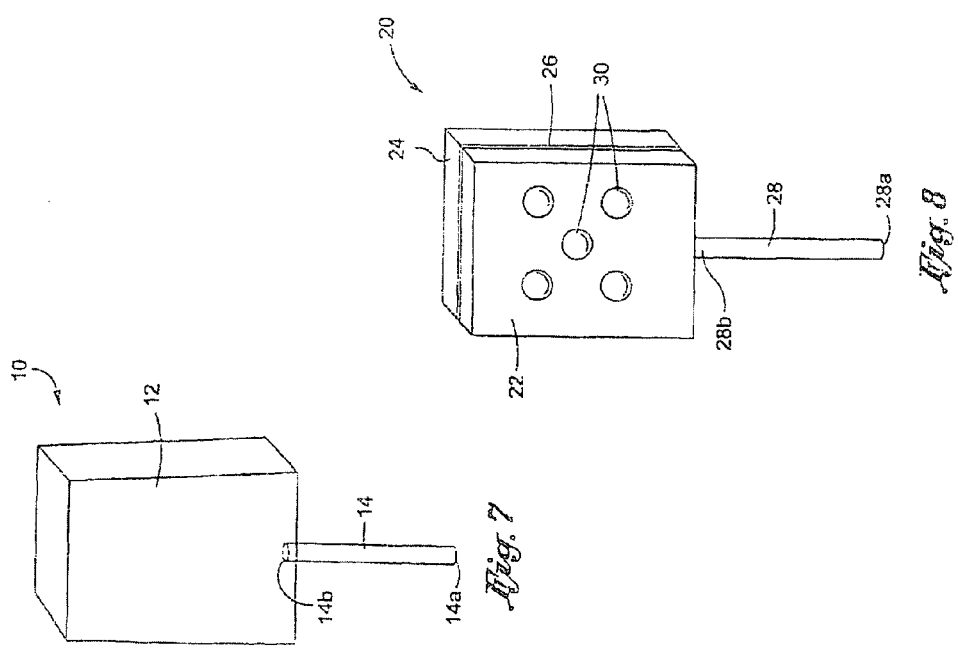

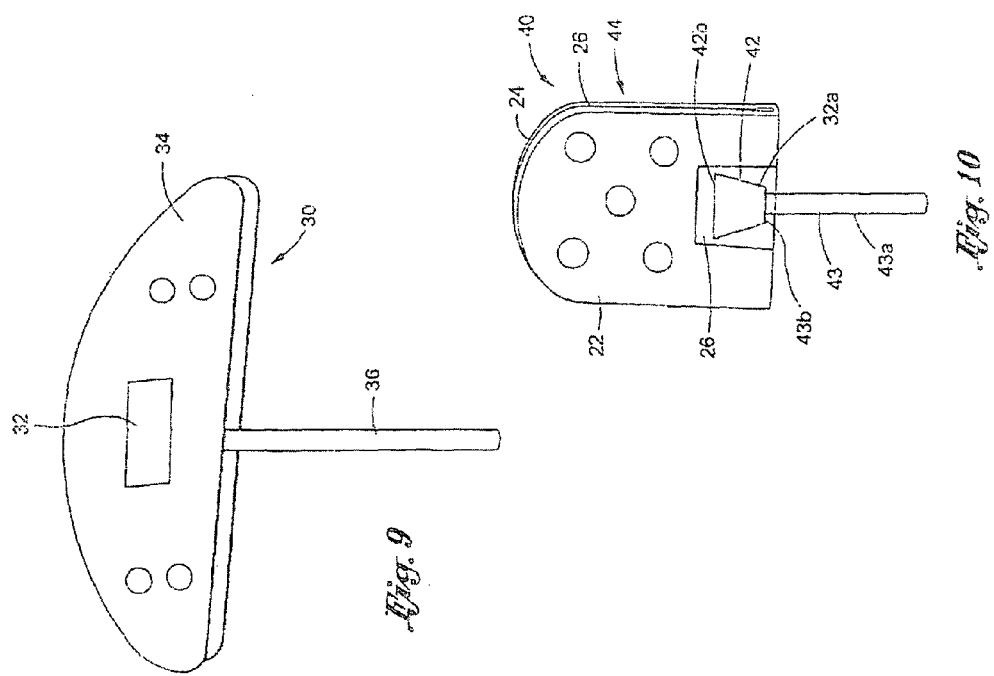

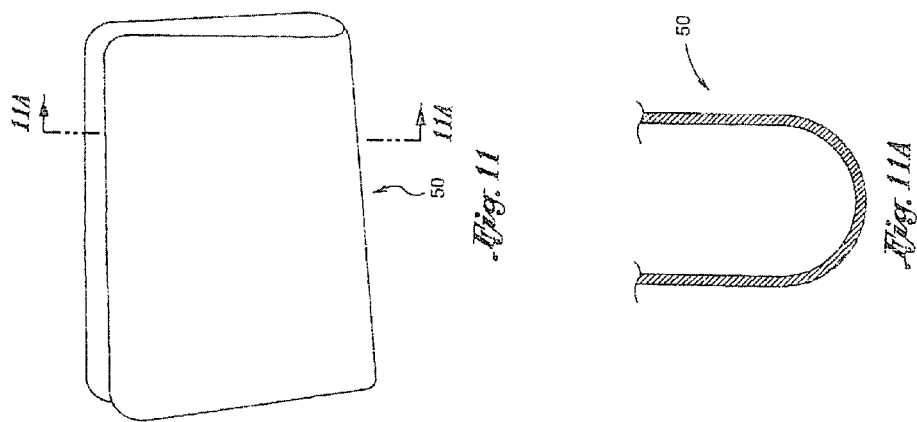

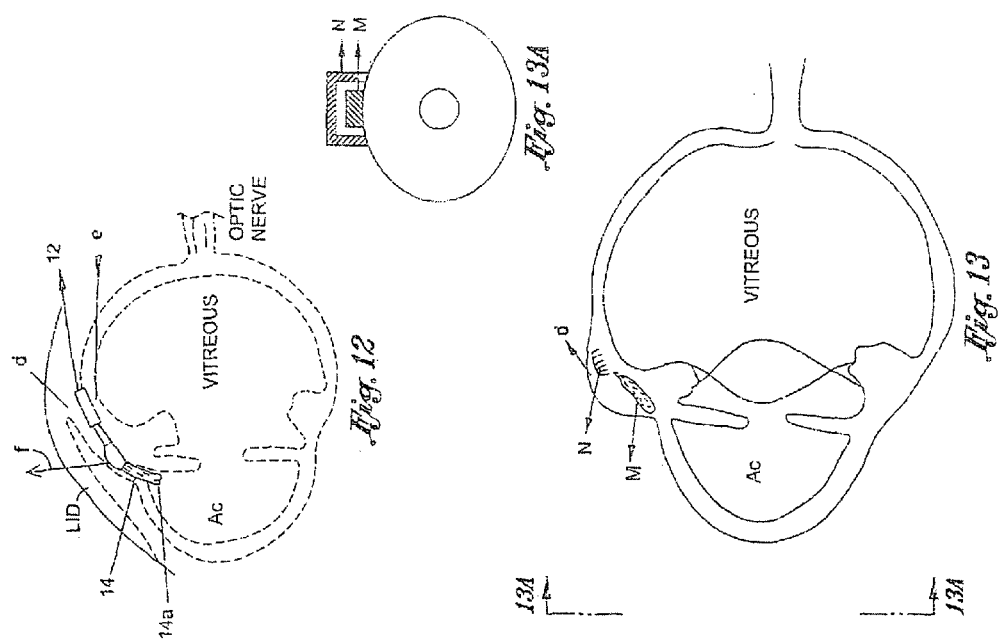

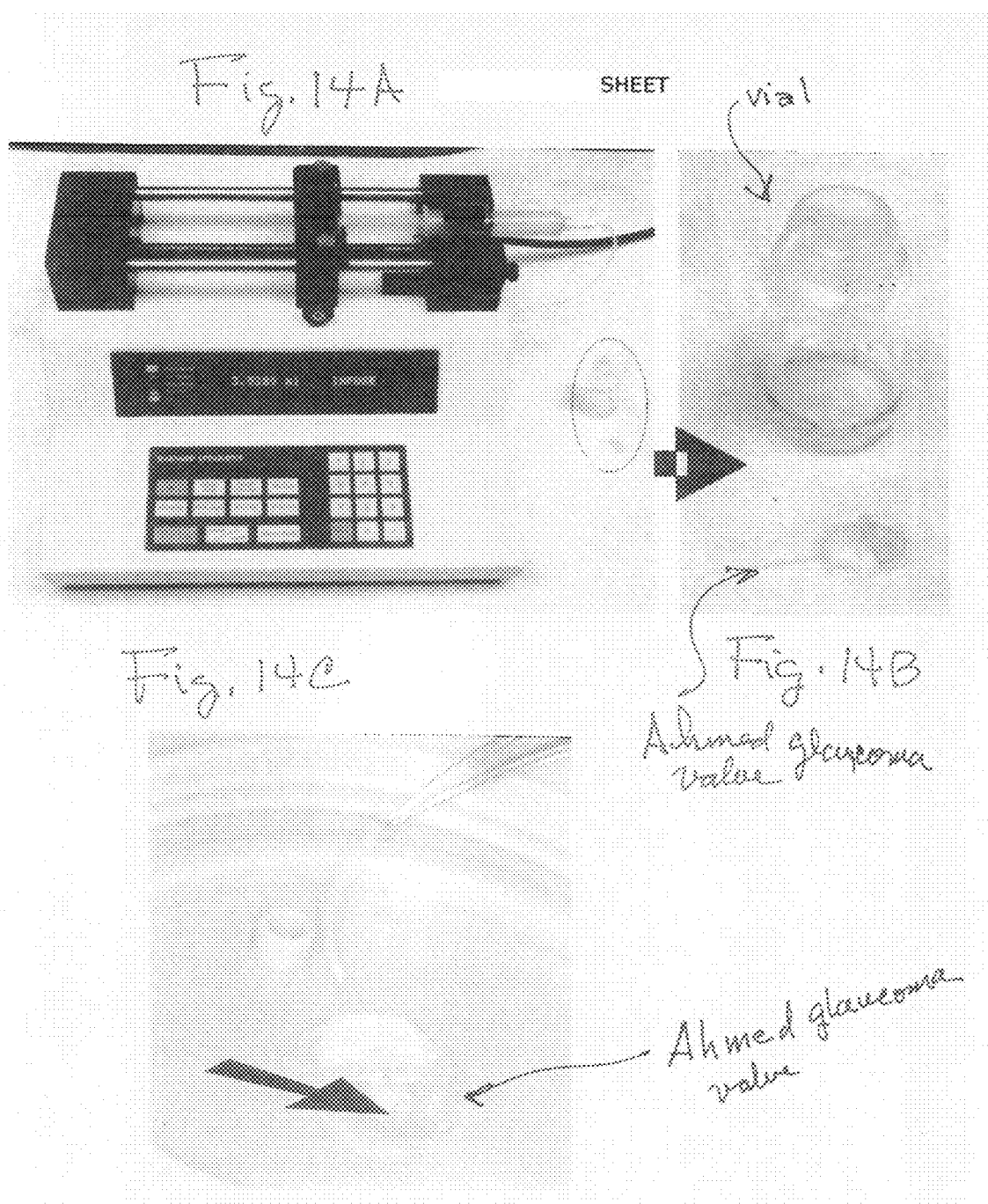

DEVICE FOR DELIVERY OF ANTIFIBROTIC AGENTS AND METHOD

RELATED PATENT APPLICATIONS & INCORPORATION BY REFERENCE

This application is a continuation-in-part application of International Application No. PCT/US 2007/012253, entitled "DEVICE FOR DELIVERY OF ANTIFIBROTIC AGENTS & METHOD," filed May 23, 2007, which claims the benefit under 35 USC 119(e) of U.S. Provisional Patent Application No. 60/808,446, entitled "DEVICE FOR DELIVERY OF ANTIFIBROTIC AGENTS & METHOD," filed May 25, 2006. These related applications are incorporated herein by reference and made a part of this application, and any and all U.S. patents, U.S. patent applications, and other documents, hard copy or electronic, cited or referred to in this application are incorporated herein by reference and made a part of this application.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

The words "consisting," "consists of," and other forms thereof, are intended to be equivalent in meaning and be closed ended in that an item or items following any one of these words is meant to be an exhaustive listing of such item or items and limited to only the listed item or items.

The words "substantially" and "essentially" have equivalent meanings.

BACKGROUND

Subconjunctival fibrosis is a major complication associated with eye surgery. While several surgical procedures and medical implants are available to treat a number of diseases and disorders of the eye, resultant tissue fibrosis often leads to unsatisfactory post-operative outcomes.

Glaucoma is a multifactorial optic neuropathy in which there is a characteristic acquired loss of retinal ganglion cells and atrophy of the optic nerve. Major risk factors for glaucoma include elevated intraocular pressure, positive family history, African heritage, and older age. Reduction and control of the intraocular pressure remains the main stay of treatment in the management of glaucoma. The increase in the intraocular pressure is thought mainly due to outflow resistance. Elevated intraocular pressure can be reduced pharmacologically, following surgical filtration procedures (GFS) or by the use of glaucoma drainage devices (GDD). The success rate of these operations is about 70-80% at one year and 40-50% at five years.

Excessive postoperative fibrosis at the wound site significantly reduces surgical success following glaucoma surgery. Pharmacological attempts to prevent fibrosis following glaucoma surgery have thus far proven unsatisfactory. Topical steroids have been the mainstay for suppressing the inflammatory/fibrous reaction that follows the various glaucoma filtering surgeries, but with variable results. The use of antifibrotic medications or agents such as, for example, 5-fluorouracil (5-FU) and mitomycin-C (MMC), help prevent the postsurgical fibrosis and improve the surgical outcomes following trabeculectomy operation (85-90% at one year compared to 70% without these agents). However, the current technique of delivering the MMC or 5-FU in the form of soaking a small wedge of sponge in a given concentration of the drug and applying to the operation site for variable time periods before washing the drug from the surgical site leads to inconsistent results.

The inflammatory/fibrous reaction that follows an operation implanting a glaucoma drainage device differs from that of trabeculectomy in that the inflammatory reaction is ongoing probably due to the biomaterial of the glaucoma drainage device. This leads to bleb encapsulation and elevated intraocular pressures in both the short term, that is, in the hypertensive phase and in the long term leading to elevated intraocular pressure and failure of the operation. The failure rate for the glaucoma drainage devices has been reported at 10% per post-operative year, thus reaching 50% failure rate in 5 years.

Antifibrotic agents have also been used during glaucoma drainage device implant operations, but with variable and questionable results. Topical application of such medications at the time of surgery appears to be less effective 7-9 mm from the limbus for such implant operations compared to the effects seen at the limbus during a trabeculectomy operation. It is therefore possible that one-time application of these agents may not be sufficient to decrease the chances of long-term fibrous reaction that occurs following an implant operation.

In the recent past, non-penetrating filtering procedures like the viscocanulostomy and deep sclerectomy with or without a collagen implant are gaining popularity as a means of controlling the intraocular pressure, at the same time avoiding the immediate postoperative complications of a penetrating filtering procedure like the trabeculectomy such as hypotony, flat anterior chamber, choroidal effusions etc. The success rate of these operations, however, is less than 50% at 12 months because of scar tissue formation.

Canaloplasty is a form glaucoma surgery in which the Schlemm's canal is dilated 360° using a microcatheter (iSciences Interventional, Calif.) followed by the placement of a stent (10-0 Prolene) to exert tension on the dilated canal. The long-term results of this operation are still unknown. Schlemm's canal is a circular channel in the eye lined with a single layer of vascular-derived endothelial cells that transports 2-3 microliters of aqueous humor per minute from the anterior chamber to the venous blood supply. By microscopy, the canal measures between 190-350 microns in average diameter in human eyes. The canal serves as the final barrier before aqueous humor enters systemic circulation. This tissue has been extensively studied because of its importance in various ocular pathologies, including glaucoma. Canaloplasty procedure is one of the first procedures to enhance the aqueous drainage through the canal by mechanical stretching. However, the long-term success of this procedure (currently unknown) may be restricted because of reactionary fibrosis. This may be prevented by the use of a slow release drug coated stent (similar to the cardiac stents).

The inflammatory/fibrous reaction that follows implant operations defers from that of the trabeculectomy operation in that the inflammatory reaction is on going, probably due to the biomaterial that makes up the implanted glaucoma drainage device and the micro-motion exhibited by an end-plate with ocular movements and the presence of the aqueous medium in the subconjunctival space and a lot of other factors that are not well understood at the present time.

In glaucoma filtration non-penetrating surgery (NPS), excessive postoperative scarring at the wound site significantly reduces surgical success. Pharmacological attempts to prevent fibrosis following glaucoma surgery have thus far proven unsatisfactory. Topical steroids have been the mainstay for suppressing the inflammatory/fibrous reaction that follows the various glaucoma filtering surgeries, but with variable results. The use of antifibrotic agents such as, for example, 5-FU and MMC help prevent the postsurgical fibrosis and improve the surgical outcomes. However, the current technique of delivering 5-FU and MMC in the form of soaking a small wedge of sponge in a given concentration of the medication and applying to the operation site for a variable time period before washing the medication from the surgical site leads to inconsistent results. Therefore, there is a need for more specific treatments directed against the inflammatory/fibrous reaction both in terms of the ability to deliver the medication in a dose dependent and predictable fashion. Desirably such treatment may also be able to deliver new antifibrotic agents having less associated problems than the current ones in use.

SUMMARY

My ophthalmological device and method of inhibiting inflammatory cell proliferation have one or more of the features depicted in the illustrative embodiments discussed in the section entitled "DETAILED DESCRIPTION OF SOME ILLUSTRATIVE EMBODIMENTS."

My ophthalmological device and method provide sustained, slow release over a prolonged period of an antifibrotic agent that decreases fibrosis formations either around an implanted ocular device or within and around an area of surgical intervention. My ophthalmological device includes an implant member carrying the antifibrotic agent that is inserted into a wound in an eye produced by surgery. The member may comprise a porous or non-porous material and it may or may not be bio-degradable. The slow release of the antifibrotic agent from the member retards the fibrous reaction and thus enhances the success rate of the operation. The claims that follow define my invention; however, without limiting the scope of my invention as expressed by these claims, in general terms, some, but not necessarily all, of the features of my device and method are:

One, the antifibrotic agent is released slowly over a prolonged period when the implant member is inserted into a wound in an eye. The prolonged period may be in excess of 1 week and may be released at a rate of substantially from 0.03 to 0.09 milligrams per hour.

Two, the surface of the implant member may be coated with the antifibrotic agent, and this antifibrotic agent may be selected from the group consisting of Mitomycin-C, 5-Flurouracil, Rapamycin, a transforming growth factor (TGF) antibody, a form of corticosteroid, an immunesuppresive agent, and heparin. The antifibrotic agents in this group do not necessary perform equally when used in eye surgery of manuals, and in particular, humans. The transforming growth factor (TGF) antibody may be selected from the group consisting of TGF-B 2 monoclonal antibody, Interlukin 1 or 6 antibody, and a cytokine antibody. The form of corticosteroid may be dexamethasone, and the immunesuppresive agent may be selected from the group consisting of cyclosporin and FK57.

Three, the implant member may comprise a porous polymeric material, which may have a width substantially from 4 millimeters (mm) to 15 mm, a length substantially from 4 mm to 15 mm, and a thickness greater than 0.25 mm, for example, substantially from 0.25 mm to 1.00 mm. This porous polymeric material may be a P-HEMA matrix and it may be bio-degradable. For example, the bio-degradable material may be selected from the group consisting of collagen, chitosan, polysaccharides, proteins, polylactides, a polylactide and glycolic acid copolymer, polyanhydrides, and polyesters.

In one embodiment, my ophthalmological device may comprise a distribution plate including the porous polymeric member. The distribution plate may have a tube extending from it having a free end adapted to be inserted into the intraocular chamber of the eye.

In another embodiment, my ophthalmological device may comprise a pressure responsive valve including a tube extending from the valve and having a free end adapted to be inserted into the intraocular chamber of the eye.

In yet another embodiment, my ophthalmological device may comprise a stent configured and sized to be inserted into the Schlemm's canal of the eye.

The aqueous medium in the intraocular chamber flows through the tube and over or through the implant member to wash the antifibrotic agent from the member and into the wound. Alternately, my ophthalmological device may be a sheet or membrane that is inserted into the wound created during eye surgery. Or it can be a drug coated stent (such as a drug coated 10-0 Prolene) that is inserted into the Schlemm's canal at the time of the surgery.

My method delivers the antifibrotic agent into a wound produced by surgical intervention in the eye. For example, an implant member carrying the antifibrotic agent may be inserted into the subconjunctival space, and the agent is released over a prolonged period in a slow and sustained fashion to reduce postoperative fibrosis. The prolonged period may be in excess of one (1) week, for example, from about 1 to about 6 weeks. The antifibrotic agent may be released at a rate of substantially from 0.03 to 0.09 milligrams per hour. My ophthalmological device may be used where the free end of the tube is inserted into an intraocular chamber of the eye during surgery. The implant member may be inserted locally in a limbal pocket of the eye to inhibit limbal scar tissue from obstructing the eye's deep scleral pocket opening in deep sclerectomy/viscocanulostomy eye operations or trabeculectomy. The implant member may be a drug coated stent that is inserted into the Schlemm's canal (either 360° such as drug coated 10-Prolene or some other material this is bioabsorable or non-absorable) to inhibit local scar tissue formation inside the canal and also to promote increased aqueous drainage across the trabecular meshwork.

These features are not listed in any rank order nor is this list intended to be exhaustive.

DESCRIPTION OF THE DRAWING

Some embodiments of my device and method will now be discussed in detail in connection with the accompanying drawing, which is for illustrative purposes only. This drawing includes the following figures (FIGS.), with like numerals indicating like parts:

FIG. 7 is a perspective view of one embodiment of my ophthalmological device.

FIG. 8 is a perspective view of another embodiment of my ophthalmological device similar to that depicted in FIG. 7.

FIG. 9 is a modified Baerveldt implant adapted to use with my method.

FIG. 10 is a modified Ahmed glaucoma valve adapted to use with my method.

FIG. 11 is a perspective view of another embodiment of my ophthalmological device.

FIG. 11A is a cross-sectional view taken along line 11A-11A of FIG. 11.

FIG. 12 is a cross-sectional view showing my ophthalmological device surgically implanted into an eye.

FIG. 13 is a cross-sectional view showing my device illustrated in FIG. 11 surgically implanted into a closed wound.

FIG. 13A is an end view taken along line 13A-13A of FIG. 13.

FIG. 14A is a photograph of a syringe pump and other devices used to emulate the flow of aqueous through a modified Ahmed valve.

FIG. 14B is an enlarged photograph taken along line 14B of FIG. 14A showing a vial in which fluid was collected after flow through the modified Ahmed valve. The Ahmed glaucoma valve with attached p(HEMA)-MMC disk is shown in the foreground.

FIG. 14C is an enlarged photograph of a modified Ahmed glaucoma valve.

DETAILED DESCRIPTION OF SOME ILLUSTRATIVE EMBODIMENTS

General

Figure 1:
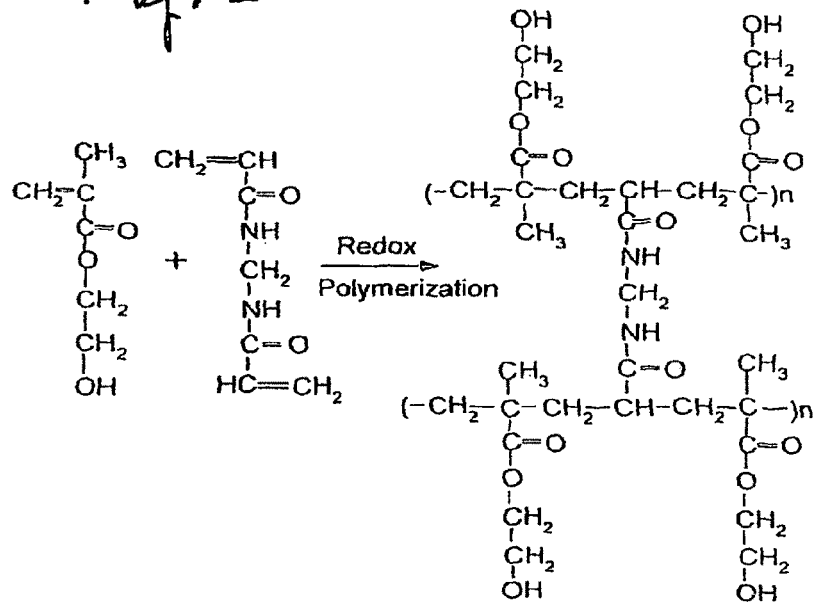
FIG. 1 depicts the synthesis of P-HEMA hydrogel with incorporated MMC using a redox polymerization method.

My ophthalmological device and method inhibits inflammatory cell proliferation to prevent fibrous tissue formation and prevent growth of fibrous tissue after eye surgery by placing in the vicinity of a wound created during surgery a member carrying an antifibrotic agent released into the wound slowly over a prolonged period. The aqueous liquid in contact with the member washes from the member or dissolves the antifibrotic agent.

The member may be a component of an implanted ophthalmological device such as, for example, the Baerveldt distribution plate disclosed in U.S. Pat. No. 5,476,445 or the Ahmed glaucoma valve disclosed in U.S. Pat. No. 5,071,408 or Schlemm stent disclosed in U.S. Pat. No. 6,464,724. It may comprise a porous material with the antifibrotic agent retained in its pores. Or, it may be or non-porous polymeric material having a surface coated with the antifibrotic agent. The polymeric material may be a bio-degradable material may be naturally occurring, for example, polymers such as collagen, chitosan, polysaccharides (starch sugar, and cellulose), and proteins, or synthetic, for example, polylactides (PLA) and its copolymer with glycolic acid (PLGA), polyanhydrides, and polyesters.

My method may be used in eye surgery such as, for example, a trabeculectomy or implanting drainage device such as, for example, the Baerveldt distribution plate or the Ahmed valve. Inhibiting fibrous tissue formation enhances the success of either implanting drainage devices or in non-penetrating surgery. The member may be inserted locally in a limbal pocket of the eye to inhibit limbal scar tissue from obstructing the eye's deep scleral pocket in deep sclerectomy/viscocanulostomy eye operations or inside the Schlemms' canal during surgeries such as canaloplasty.

Experiments

The following experiments were conducted to test delivering antifibrotic agents to wounds resulting from eye surgery:

1. To create a devices or membrane that is loaded with an antifibrotic agent that is released slowly over a 1-3 week period and test its efficacy in the lab using cultured fibroblasts in a Petri dish model.

2. To test a simple plate-tube model of a device having a portion coated with Mitomycin C in a rabbit model and study the histology of the bleb.

3. To test a NPS membrane in a rabbit model.

The following are antifibrotic agents: Mitomycin C, 5-Flurouracil, Rapamycin, transforming growth factor (TGF) antibodies (specifically, TGF-B 2 monoclonal antibody, Interlukin 1 or 6 antibody or other cytokine antibodies), a form of corticosteroid such as, for example, dexamethasone, immunesuppresive agents such as, for example, cyclosporin or FK57, and heparin.

Delivery methods varied: (1) local delivery of such antifibrotic agents from the surface an end-plate of a glaucoma drainage device; (2) delivery from the surface of a thin biomaterial membrane (both degradable and non-degradable) inserted at the time of non-penetrating surgery including canaloplasty (NPS membrane); (3) delivery involving a co-mixture with polymers (both degradable and non-degradable) to hold the antifibrotic agent to the glaucoma drainage device or to the membrane to be used at the time of the non-penetrating surgery; (4) delivery by entrapping the antifibrotic agent in the material comprising the glaucoma drainage device or the NPS membrane modified to contain microspores or channels; (5) delivery by including covalent binding of the antifibrotic agent to the glaucoma drainage device or the NPS membrane via solution chemistry techniques such as, for example, via the Carmeda process or dry chemistry techniques, for example, vapor deposition methods such as rf-plasma polymerization; and (6) combinations of these delivery methods.

Development of a Rabbit Model to Assess Fibrosis Around the Glaucoma Drainage Device Based on Different Biomaterials Because as many as 30% of eyes undergoing GDD implantation develop excessive scar tissue, developing a slow-release ocular drug delivery system is highly desirable. The initial experiments focused on creation of a rabbit model to study the effects of various biomaterials on the degree of fibrosis. This rabbit model was effective in modeling the extent of fibrosis around the end-plates of different commercially available. Subsequent clinical studies confirmed positive results with the rabbit model using the antifibrotic drug MMC incorporated into a p(HEMA)-based drug release device. The p(HEMA) polymer was washed to remove low molecular weight toxicants that remained after polymerization and the MMC was subsequently loaded into the matrix by a novel mechanism. This polymer was able to release the drug on contact with water, which is ideal for glaucoma surgeries as the aqueous escaping the eye through the surgical tract would trigger the release of the drug, which would then decrease fibrosis around the plate. In vitro release tests were performed initially to study the rate of drug release from the matrix. Then the efficacy of the slow-release device was measured in a cell culture system, using human conjunctival fibroblasts. These results demonstrated that the p(HEMA) polymer was able to release MMC and inhibit the proliferation of the fibroblasts in a dose-dependent manner.

Experiment 1

Inhibition of Cell Proliferation by Mitomycin C Incorporated into P-HEMA Hydrogels In this Experiment 1 a device including a P-HEMA matrix was tested that releases low concentrations of mitomycin-C over a 3-week period using an in vitro model.

Materials and Methods

Materials: Neutral buffered formalin, toluidine blue, hematoxylin and eosin solution, sodium dodecyl sulfate, mitomycin C (*Streptomyces caespitosus*), reagents for tissue culture (culture medium, trypsin, antibiotics) and reagents for hydrogel synthesis (2-hydroxyethyl methacrylate, N,N'-methylene-bisacrylamide, N,N,N',N'-tetramethylethylenediamine, and ammonium persulfate) were purchased from Sigma/Aldrich (St. Louis, Mo.). Tissue culture dishes (60 mm diameter) were from Corning-Costar (Corning, N.Y.). COS-1 cells were obtained from the American Type Culture Collection (Manassas, Va.). Early passage human conjunctival fibroblasts were established in 1994 from a biopsy sample of a 43 year old white male. The primary cultures were frozen in liquid nitrogen at $2^{nd}$ passage. This cell strain does not have an infinite life span and early passage cultures ($4^{th}$-$6^{th}$ passage) were used for the present experiments. Both the COS-1 cell line and the fibroblast strain were maintained in DMEM containing 100 u/ml penicillin G, 0.25 µg/ml amphotericin B, 100 u/ml streptomycin and 10% fetal bovine serum (Hyclone Laboratories, Logan, Utah).

Hydrogel synthesis: In a typical P-HEMA hydrogel synthesis, 0.0508 g of N,N'-methylene-bisacrylamide (MBA) was dissolved in 4 ml distilled water containing 400 µL N,N,N',N'-tetramethylethylenediamine (TEMED). This was followed by the addition of 4 ml of 2-hydroxyethyl methacrylate (HEMA solution, 99%) and thorough mixing. A 1 ml aliquot of ammonium persulfate (AMP) in water (0.5 mol % with respect to HEMA monomer) was subsequently added. Following mixing of all components, the solution was cast between two sealed glass slides and allowed to react at least 12 hours at room temperature to form the hydrogel. The product was a polymer sheet approximately 2 mm thick. The reaction followed typical redox pathways. For all syntheses, the crosslinker MBA was included at a 1:100 mol ratio of crosslinker to monomer.

Mitomycin C (MMC) was loaded into the hydrogels by two different procedures. In Procedure 1, the drug was directly mixed in with the hydrogel precursors before polymerization/crosslinking. After hydrogel formation, the solid polymer hydrogel was cut into circular discs of 8 mm diameter using a trephine. The disks were sterilized by UV-irradiation for a period of 2 hours, and then used in cell culture studies. In Procedure 2, the polymer was synthesized first and cut into circular disks of 8 mm diameter. Unreacted, low molecular weight species were removed from the polymer was by repeated washing with a 50/50 (v/v) solution of distilled water and ethanol. MMC at the required concentrations was dissolved in ethanol and then incubated with the disks in standard 10 ml vials. The solvent was then slowly evaporated during which time MMC diffuses into the swollen polymer as a consequence of the concentration gradient. When all the bulk solvent had evaporated, the disks containing MMC were gently air-dried and then sterilized by UV irradiation. The use of ethanol as a solvent in drug loading procedures also helped sterilize the polymer matrix.

Measurement of polymer cytotoxicity in vitro: A single 8 mm disk of sterile polymer was affixed to the center of each 60 mm tissue culture dish with clear RTV silicone cement. The silicone cement was sterile as it came from the tube and care was taken during this procedure to maintain the sterility of both the polymer and the tissue culture dish. The cement was allowed to cure for 1-2 hours in a sterile environment, until no odor of acetic acid could be detected. COS-1 cells or conjunctival fibroblasts ($1.5 \times 10^5$ cells/60 mm culture dish) were added to the polymer-containing dishes and the cells were maintained at 37° C. in a humidified 5% $CO_2$-95% air atmosphere; culture medium was replenished on day 3 and 5 after the cells were plated. After 7 days of culture, cell accumulation in each culture dish was assessed by a modification of the method of Leavesley (Leavesley D I, Ferguson G D, Wayner E A, Cheresh D A: Requirement of the integrin beta 3 subunit for carcinoma cell spreading or migration on vitronectin and fibrinogen, J. Cell Biol. (1992) 117, 1101-1107). The culture medium was removed and the cell layer was gently washed 3 times with 5 ml of phosphate-buffered saline. The polymer piece was removed from each dish, cells were fixed for 30 minutes in 5 ml of neutral buffered formalin, then stained for one hour with 5 ml of 1% toluidine blue in neutral buffered formalin. The dye solution was removed, the cell layer was washed 4 times with 5 ml of distilled water, and the dishes were allowed to air-dry overnight at room temperature. Dye bound to the fixed cells was solubilized by the addition of 2 ml of 2% aqueous sodium dodecyl sulfate, followed by incubation for 15 minutes. The amount of dye in each dish, which was proportional to the number of cells, was measured as the absorbance at 650 nm on a Shimadzu UV-Visible spectrophotometer (Model UV-1601, Shimadzu Scientific Instruments Inc., Houston, Tex.). In some cases, the solutions had to be diluted with 2% aqueous sodium dodecyl sulfate to bring the absorbance within the linear range of the spectrophotometer. For some experiments, the dishes were photographed before the dye was solubilized. In other experiments, replicate dishes were fixed in neutral buffered formalin and then stained with hematoxylin/eosin to monitor cell morphology.

Statistical Analyses: All cytotoxicity tests were performed in quadruplicate and values reported are mean±SD. Where appropriate, the Student's t-test provided in the Microsoft Excel™ software was employed to determine statistical significance. The dose-response curve for MMC toxicity was fit using the exponential model and software contained in SlideWritePlus for Windows™, ver. 6.10.

Results

The incorporation of an antifibrotic agent into a slow release polymer could have significant advantages in slowing the fibrosis that is so often the cause of bleb failure after glaucoma surgery. A first step in the development of such polymers is the demonstration that 1) the polymer matrix itself has little or no cytotoxicity and 2) the anti-proliferative agent is released from the polymer in an active form. The hydrogels used in the present study were synthesized by a standard redox mechanism as depicted in FIG. 1. The inclusion of the crosslinker, MBA at a concentration of 1 mol % provided hydrogel sheets that were firm enough to be easily manipulated in subsequent experiments.

Cytoxicity of polymers prepared by Procedure 1: COS-1 cells (a readily available, immortalized cell line[9]) were used in preliminary experiments to establish the parameters of the study (number of cells in the initial inoculum, days in culture, number of medium changes, method of quantifying cell number). Once these parameters had been determined, the study was repeated with early passage cultures human conjunctival fibroblasts, the cell type against which these slow release polymers will ultimately be targeted. An inoculum of $1.5 \times 10^5$ cells per 60 mm culture dish produced a confluent monolayer after 7 days in culture. Two medium changes were incorporated into the protocol; these medium changes insured that nutrients did not become limiting during the experimental period and also periodically removed cytotoxins released from the polymers, in a manner analogous to the natural "flushing" of a wound site with interstitial fluids. The method of Leavesley was used in a slightly modified form to assess cell number in these experiments. Cells were cultured in the presence of test agent for 7 days, then the medium was removed and the cell layer was lightly fixed. Toluidine blue, a basic dye that binds primarily to basophilic structures, including nuclei, ribosomes, and glycosaminoglycans, was subsequently added. After extensive washing to remove unbound dye, the culture dishes were dried overnight.

Figure 2:
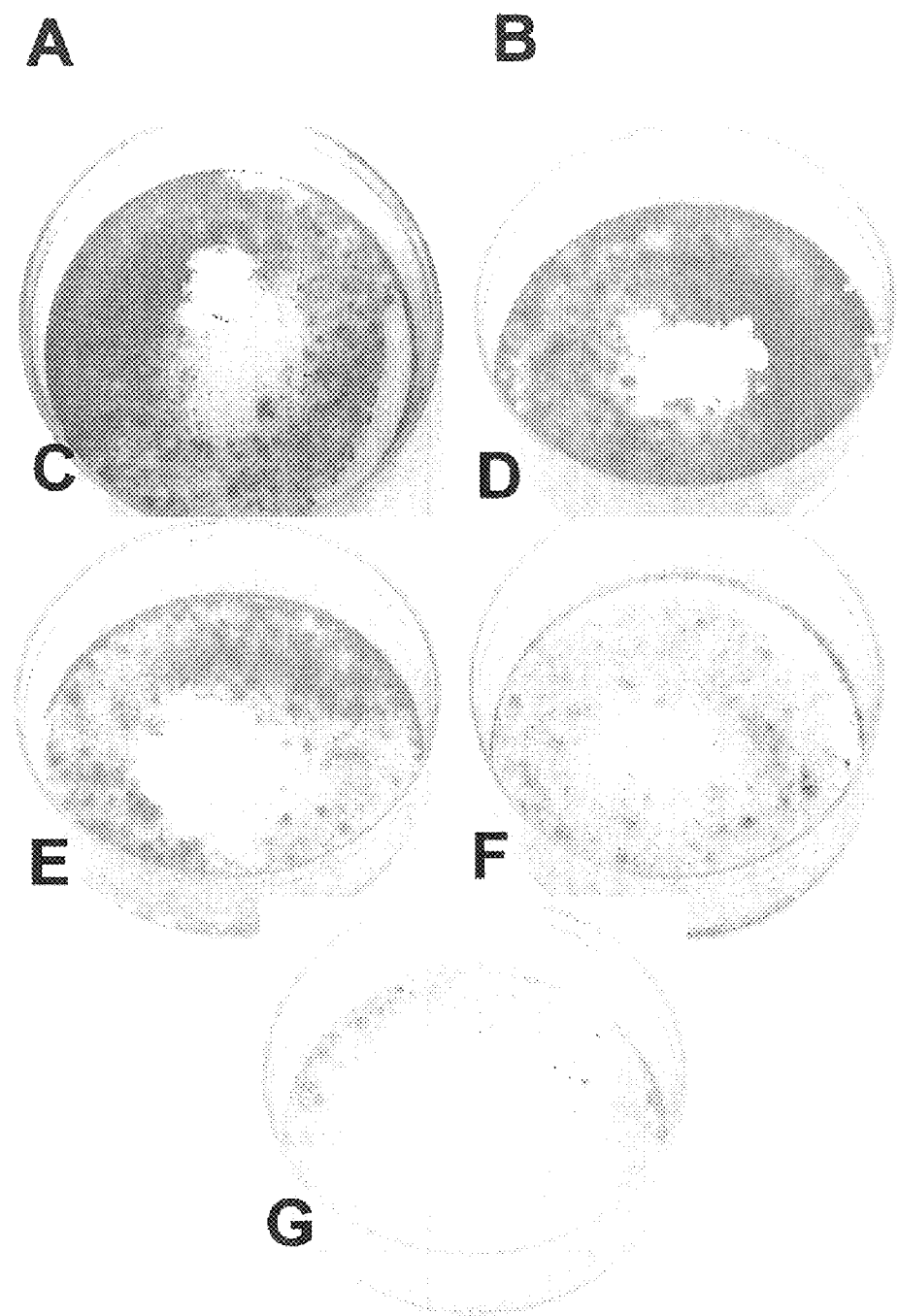
FIG. 2 shows representative photographs of cell culture dishes used for P-HEMA toxicity tests after fixation and toluidine blue staining.

FIG. 2 shows a representative sampling of fixed and stained culture dishes after a test of polymers prepared by Procedure 1. Accordingly, culture dishes (60 mm) with an affixed 8 mm disk of polymer prepared by Procedure 1 were inoculated with COS-1 cells as described above. The cultures were fixed and stained 7 days after inoculation to provide Panels A through G, FIG. 2: Panel A, no additions; Panel B, silicone cement alone; Panel C, P-HEMA hydrogel with no incorporated MMC; Panel D, P-HEMA hydrogel with 0.031 mg/g incorporated MMC; Panel E, P-HEMA hydrogel with 0.156 mg/g incorporated MMC; Panel F, P-HEMA hydrogel with 0.311 mg/g incorporated MMC; Panel G, P-HEMA hydrogel with 0.420 mg/g incorporated MMC.

Panel A shows the stained, confluent monolayer produced by COS-1 cells after 7 days in culture in the absence of a polymer sample. Panel B shows a culture dish to which the silicone cement, but no polymer has been added. Panel C shows a dish cultured for 7 days with a polymer disk that contained no added MMC, and Panels D through F show dishes which has been cultured with polymer disks containing 0.031, 0.156, 0.311, and 0.420 mg/g incorporated MMC, respectively. While the silicone cement used to affix the polymer disks had no discernible effect on cell proliferation (compare Panels A and B) it was clear from the examination of the stained dishes that even the polymer that contained no incorporated MMC was inhibiting cell proliferation.

Figure 3:
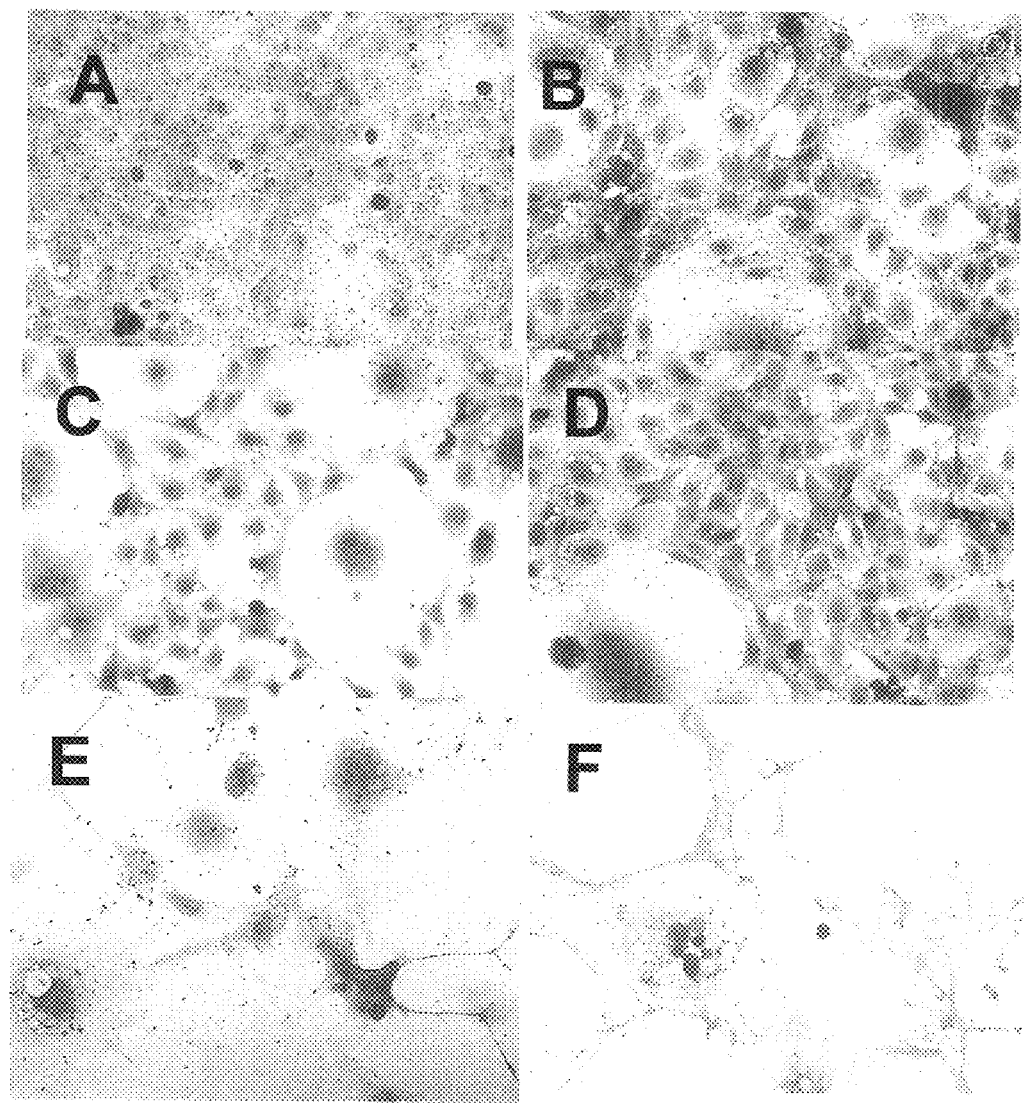
FIG. 3 shows photomicrographs of COS-1 cells cultured for 7 days in the presence or absence of hydrogel polymers.

Evidence of cytotoxicity was also observable at the cellular level, as shown by the photomicrographs in FIG. 3 including Panels A through F: Panel A, cells cultured in the absence of polymer; Panel B, cells cultured in the presence of P-HEMA hydrogel prepared by Procedure 1, with no incorporated MMC; Panels C-F, cells cultured in the presence of P-HEMA Hydrogels prepared by Procedure 1, with incorporated MMC at the concentrations (mg/gram of gel) of 0.031, 0.156, 0.311, and 0.42, respectively. All photomicrographs Prepared at an identical magnification (approximately 300×).

COS-1 cells cultured in the absence of polymer (Panel A, FIG. 3) formed a confluent monolayer of uniformly shaped cells, as did cells cultured in dishes containing silicone cement alone (data not shown). Cells cultured in the presence of polymer, however, showed obvious signs of distress, including irregular shaped and giant cells and the presence of vacuoles (Panels B-F, FIG. 3). Note the morphological changes in those cells cultured with a polymer sample that lacked incorporated MMC (Panel B, FIG. 3). The obvious toxicity of the polymer matrix made it difficult to distinguish the effects of the polymer from those of the incorporated MMC, especially at the lower MMC concentrations (see Panels C and D, FIG. 3). The effect of the polymers on cell proliferation was quantified by solubilizing the toluidine blue in the stained dishes and measuring the absorbance in a spectrophotometer.

A single 8 mm disk of polymer prepared by Procedure 1 was affixed to each culture dish with silicone cement and cells were fixed and stained 7 days after inoculation, as described above. After solubilization of the cell-bound dye, the color (quantified as absorbance at 650 nm) was a measure of the number of cells in each dish. "Control" indicates data from cells inoculated into culture dishes with no additions; "Cement", indicates data from cells inoculated into dishes containing silicone cement, but no polymer. Panel A, FIG. 3, COS-1 cells; Panel B, FIG. 3, human conjunctival fibroblasts. Data is presented as mean±SD (n=4); All test groups were compared to the hydrogel sample with no incorporated MMC using Student's t-test, *, $p \leq 0.005$.

Figure 4:
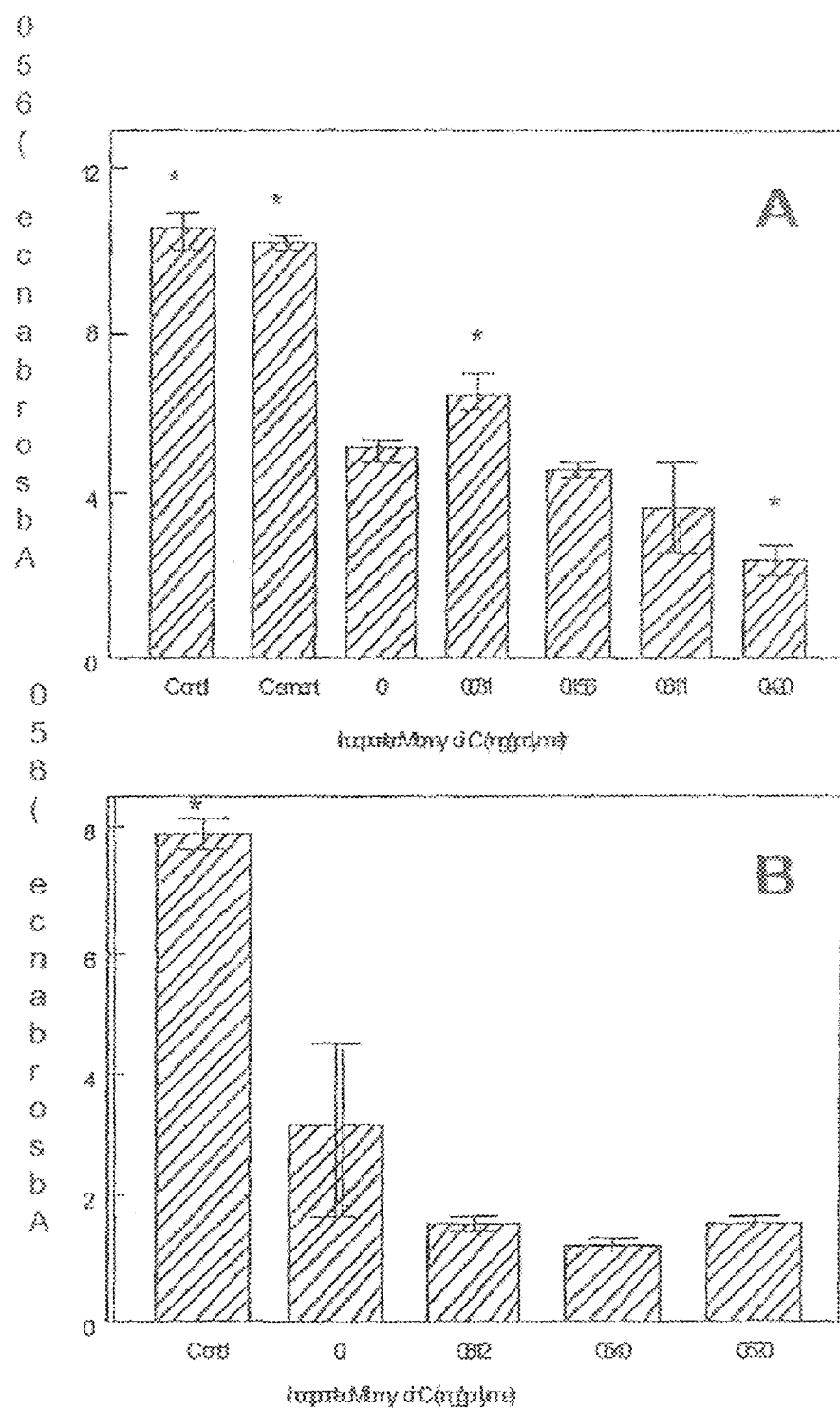
FIG. 4 shows the sensitivity of COS-1 and early passage human conjunctival fibroblasts to P-HEMA hydrogels.

FIG. 4, graph A, shows the absorbance values obtained with COS-1 cells cultured for a 7-day experimental period. As expected from the visual inspection of the stained dishes, cells cultured in the presence of silicone cement achieved an absorbance equivalent to that in dishes with no additions. The presence of polymer that contained no MMC in the culture dish reduced the number of cells after 7 days in culture to 48% of that observed in control cultures. In fact, the toxicity of the polymer matrix was so high that it obliterated any dose-response relationship when increasing amounts of MMC were incorporated into the hydrogel. Only those dishes containing polymer with the highest MMC concentration (0.420 mg/g polymer) had a significantly lower number of cells than did the dishes containing the polymer with no MMC. The toxicity of the polymer matrix was even more pronounced when early passage conjunctival fibroblasts were used in these experiments, as shown in FIG. 4, graph B. The effect of the polymer matrix on cell growth was so profound that incorporation of MMC into the polymer had no additional cytotoxic effect.

Figure 5:
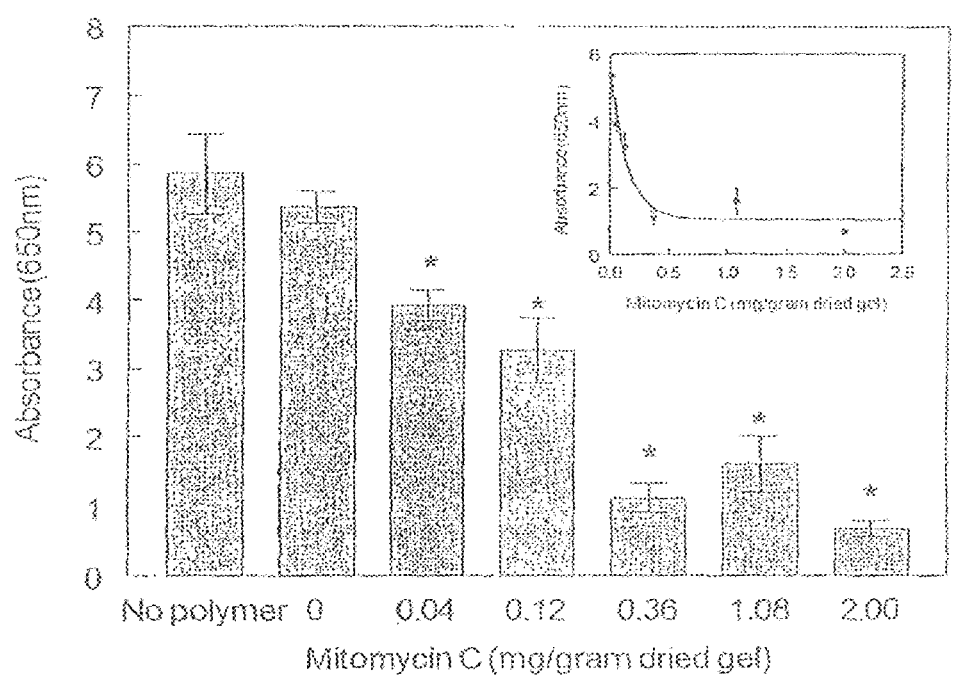
FIG. 5 shows the sensitivity of early passage human conjunctival fibroblasts to salt-free P-HEMA hydrogels.

Cytotoxicity of polymers prepared by Procedure 2: The low molecular weight components present in the polymer matrix (unreacted monomer, TEMED, APS) responsible for the cytotoxicity of the polymers prepared by Procedure 1 were hypothesized. A method for removing these components from the polymer matrix before MMC was incorporated was developed. In preliminary experiments with COS-1 cells, polymer matrix prepared by Procedure 2 had no detectable cytotoxicity in the absence of MMC (data not shown). The human conjunctival fibroblasts were more sensitive than COS-1 cells to these low molecular components. As illustrated in FIG. 5, the sensitivity to polymers prepared by Procedure 2 using this cell line were quantified A single 8 mm disk of polymer was affixed to each culture dish with silicone cement and cells were fixed and stained 7 days after inoculation, as described in Methods. After solubilization of the cell-bound dye, the color (measured as absorbance at 650 nm) was a measure of the number of cells in each dish. "Control" indicates data from cells inoculated into culture dishes with no additions. Data is presented as mean±SD (n=4); All test groups were compared to the hydrogel sample with no incorporated MMC using Student's t-test, *, $p \leq 0.016$.

A salt-free polymer matrix with no incorporated MMC has no significant effect on the proliferation of the fibroblasts. Incorporated MMC inhibited cell proliferation in a dose-dependent fashion. The dose response to MMC could be fit to an exponential (see FIG. 5 insert); the $r^2$ value for the fit was 0.95 and the concentration of MMC that inhibited 50% of cell proliferation ($IC_{50}$) was calculated to be 0.15 mg/g dried gel.

Figure 6:
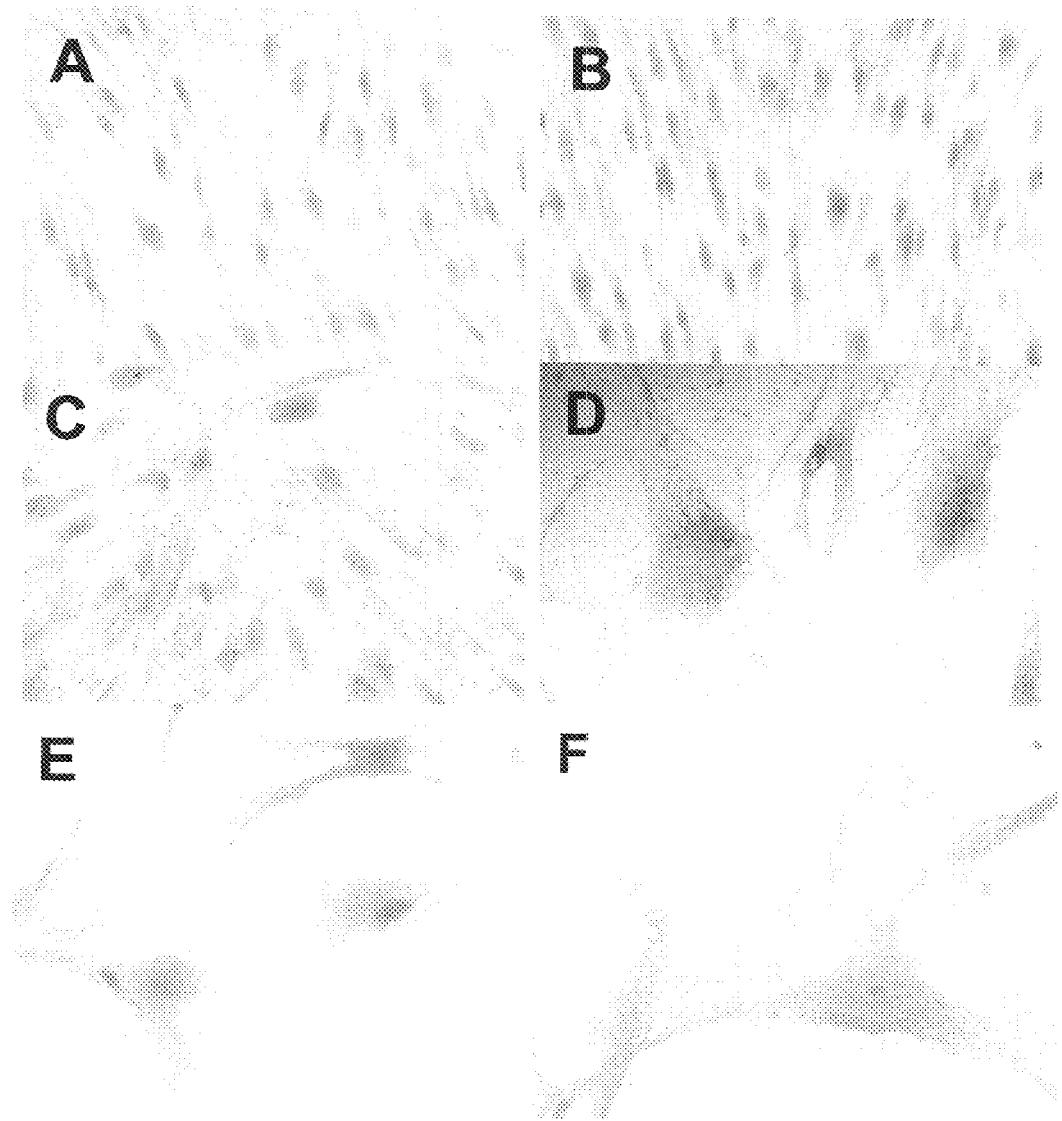
FIG. 6 shows photomicrographs of human conjunctival fibroblasts cultured for 7 days in the presence or absence of salt-free hydrogel polymers.

The morphology of fibroblasts cultured in the presence or absence of the polymer samples was also assessed, as shown in FIG. 6. In FIG. 6, Panel A shows cells cultured in the absence of polymer; Panel B shows cell cultured in the presence of P-HEMA hydrogen prepared by Procedure 2, with no incorporated MMC; Panels C-F shows cells cultured in the presence of P-HEMA hydrogels with incorporated MMC at the concentrations (mg/gram of gel) of 0.04, 0.12, 0.36, and 2.0, respectively. All photomicrographs were prepared at an identical magnification (approximately 300×).

As expected from the proliferation experiments, culture for 7 days in the presence of polymer with no incorporated MMC had little or no effect on the morphology of the cells (compare Panels A and B in FIG. 6). As increasing quantities of MMC were added to the polymer samples the cells, the morphology became more and more atypical, as shown in Panels C-F of FIG. 6.

Experiment 2

A white albino rabbit was used for the experiment sedated with IM ketamine 35 mg/kg and xylazine 5 mg/kg per vivarium protocol. The area of the eye was shaved to prevent hair from contaminating the field. The field was prepped with betadine, and draped in a sterile fashion. Topical anesthesia with proparicane 0.5% was used to prevent any further discomfort. After this is done, the supero-temporal sub-conjunctival space was exposed opening the conjunctiva with wescott scissors. Once the tenon's tissue was separated a glaucoma drainage device end-plate measuring 1.5 mm×1.5 mm was inserted into the space and secured to the underlying sclera with two interrupted sutures. The tube attached to the plate was then inserted into the anterior chamber through a 23 gauge needle tract. The conjunctiva was closed with a running chromic suture. The animal was treated with topical tobradex ointment twice a day to prevent infection for 1 week. At one week after the surgery, clinical examination has revealed a large avascular cystic bleb on the surface of the end plate. The animal was euthanized per vivarium protocol on day 8. The eye was enucleated taking care not to disturb the end plate or the bleb. The eye was injected with 10% formalin and preserved in a formalin jar. It was sent for histological examination by an independent ocular pathologist well versed with rabbit histology.

Pathology

The rabbit eye was in fixative and measured 17×17×16 mm. A "plastic" exoplanted reservoir was present superiorly measuring approximately 12 mm in largest dimension. This was removed before opening the globe. The eye was opened through the plane of the exoplant device. The eye was phakic and the retina attached. Microscopic sections show edematous conjunctival tissue superiorly (bleb) with minimal round cell infiltration. The inner surface of the space formed between the superior conjunctiva and episclera was lined by fibinrous material containing few cells. There were no areas of granulomatous inflammation or necrosis noted. There was no vasculitis. There was no pathologic change noted inside the eye.

Summary of Experiment 2

In order to test the hypothesis that a slow release drug delivery system using P(HEMA) loaded with Mitomycin C would decrease the fibrosis, a glaucoma drainage device was created in the laboratory that consisted of a 13 mm 10 mm P(HEMA) plate loaded with MMC (2 mg/dry weight of the polymer) attached to a silicone tube. This plate and tube were implanted into the rabbit eye (using standard surgical techniques). The results demonstrated significant reduction in the fibrosis with a resulting avascular bleb formation at the end of 1 week. This experiment proved that the concept of slow release drug delivery system worked in the rabbit model.

Devices

FIG. 7 schematically depicts one embodiment of my ophthalmological device identified by the numeral 10. The ophthalmological device 10 may be used to treat glaucoma and includes a distribution plate 12 carrying an antifibrotic agent and a tube 14 attached to the plate 12 near an inner end 14b so fluid exiting this inner end flows onto the plate. The plate 12 may be solid or porous, and its dimensions may be, for example, substantially 8 mm×8 mm×0.5 mm. If the plate is solid, the antifibrotic agent is applied as a coating to the exterior surface of the plate. If the plate is porous, the antifibrotic agent is absorbed in the pores of the plate material. Both the plate 12 and the tube 14 may be made of silicone. The hydrogel prepared as discussed above, or another material including an antifibrotic agent, is applied to the plate 12 in a sufficient quantity so the antifibrotic agent is released slowly over a prolonged period, for example, 1-3 weeks, when inserted into a wound in an eye produced by surgery. When implanted in a patient's eye to treat glaucoma in accordance with conventional surgical procedures, the aqueous humor from the eye' intraocular anterior chamber AC flows into the open end 14a of the tube 14 and over the plate 12.

As illustrated in FIG. 12, the plate 12 is sutured to the bare sclera d under the conjunctival/Tenons' pocket approximately 7-10 mm from the limbus with the help of non-absorbable sutures such as prolene or nylon. Then the open end 14a of the tube 14 is inserted into the anterior chamber AC through a needle tract. The scleral portion of the tube is then covered with scleral or pericardial patch graft f to prevent future tube conjunctival erosion, and secured to the surrounding sclera e. Then, the conjunctiva is secured to the limbus. The aqueous humor exits the anterior chamber AC through the inner end 14b flowing across the plate 12 and into the subconjunctival space d and is absorbed by surface blood vessels.

Another embodiment of my ophthalmological device identified by the numeral 20, also used to treat glaucoma, is schematically depicted in FIG. 8. The ophthalmological device 20 includes a pair of silicone plates 22 and 24 having a sheet of matrix material 26, for example, the P-HEMA-Drug matrix carrying the antifibrotic agent, is sandwiched between the pair of plates. A silicone tube 28 has its inner open end 28b in contact with the matrix material 26 and its outer open end 28a is adapted to be placed into the eye as discussed above so the eye's aqueous humor may flow into the sheet of matrix material 26. The plate 22 has a plurality of hole 30 therein. The dimensions of the plates 22 and 24 may be, for example, 8 mm×8 mm×0.5 mm. The dimensions of the sheet of matrix material 26 may be, for example, 8 mm×8 mm×0.5 mm.

The ophthalmological device 20 is implanted in an eye to treat glaucoma in essentially the same manner as discussed above in connection with the device 10.

FIG. 9 schematically depicts yet another embodiment of my ophthalmological device identified by the numeral 30. This device 30 is a conventional Baerveldt implant device modified by inserting a sheet of material 32 carrying the antifibrotic agent onto the surface of a distribution plate 34 of the Baerveldt implant device. A tube 36 attached to the distribution plate 34 provides a passageway for the aqueous humor flowing from the eye to wash the antifibrotic agent from the sheet of material 32 when the device 30 is implanted in an eye essentially in the same manner as discussed above.

FIG. 10 schematically depicts still another embodiment of my ophthalmological device identified by the numeral 40. This device 40 includes an Ahmed glaucoma valve 42 and a distribution plate 44 similar to the device 20 including a pair of silicone plates 22 and 24 having a sheet of matrix material 26 carrying the antifibrotic agent sandwiched between the pair of plates. A tube 43 has one open end 43b in communication with an inlet 42a of the valve the valve 42 that opens at an outlet end 42b in response to a differential in pressure across the valve. The outlet end 42b is in contact with the sheet of matrix material 26, so, when the ophthalmological device 40 is implanted as discussed above, the aqueous humor from the eye flows first through the tube 43 and out the open outlet end 42b, washing the antifibrotic agent from the sheet of matrix material 26.

FIGS. 11 and 11A schematically depicts still another embodiment of my ophthalmological device identified by the numeral 50. This ophthalmological device 50 is made of a biodegradable material in the form of a sheet or plate 52 folded, cut, or otherwise formed into a suitable shape as required for placement in a wound created during eye surgery. As shown in FIG. 11A, the sheet or plate 52 may have a substantially U-shaped configuration, which is a convenient shape for use in several eye surgical procedures. The sheet or plate 52 may have dimensions of 15 mm×15 mm×0.25 mm. This sheet or plate 52 is impregnated or coated with the antifibrotic agent in a sufficient amount to release slowly over a 1-3 week period after surgery. After this release period, the sheet or plate 52 disintegrates without any toxic reaction or other side effects. As illustrated in FIGS. 13 and 13A, non-penetrating surgery may use the sheet or plate 52. Fluid from the wound created by the surgery contacts the sheet or plate 52 to slowly release the antifibrotic agent.

Figure 13B:
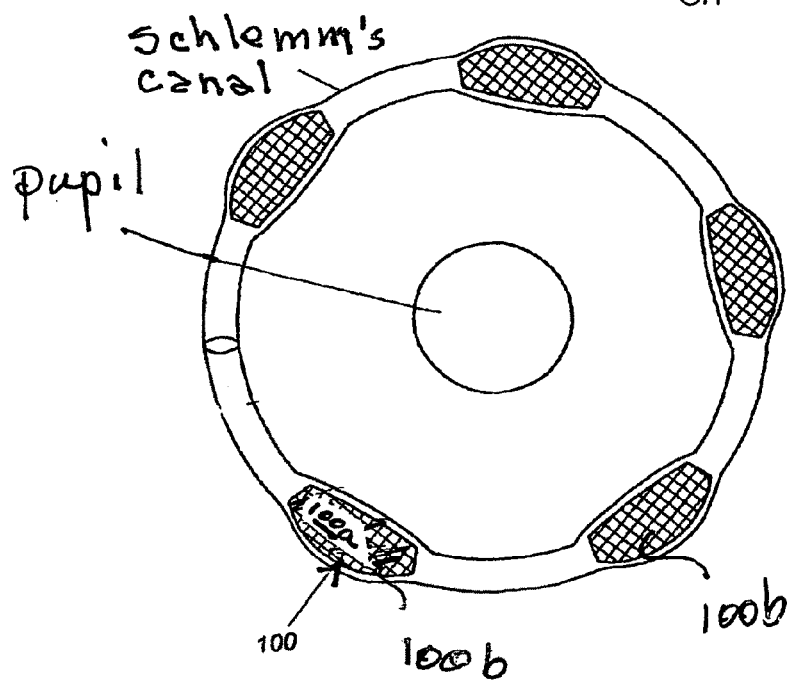
FIG. 13B is a schematic illustration showing the anatomic relationships (not to scale) of my stent inserted into the Schlemm's canal of the eye.

FIG. 13B shows a Schlemm stent 100 having its exterior surface 100a coated with an antifibrotic agent 110b in a manner described above so that the antifibrotic agent is released slowly over a period in excess of one week. A porous p(HEMA) sheet may or may not be used.

Experiment 3

Incorporation of the p(HEMA) Drug Delivery System into a Commercial GDD

Figure 15:
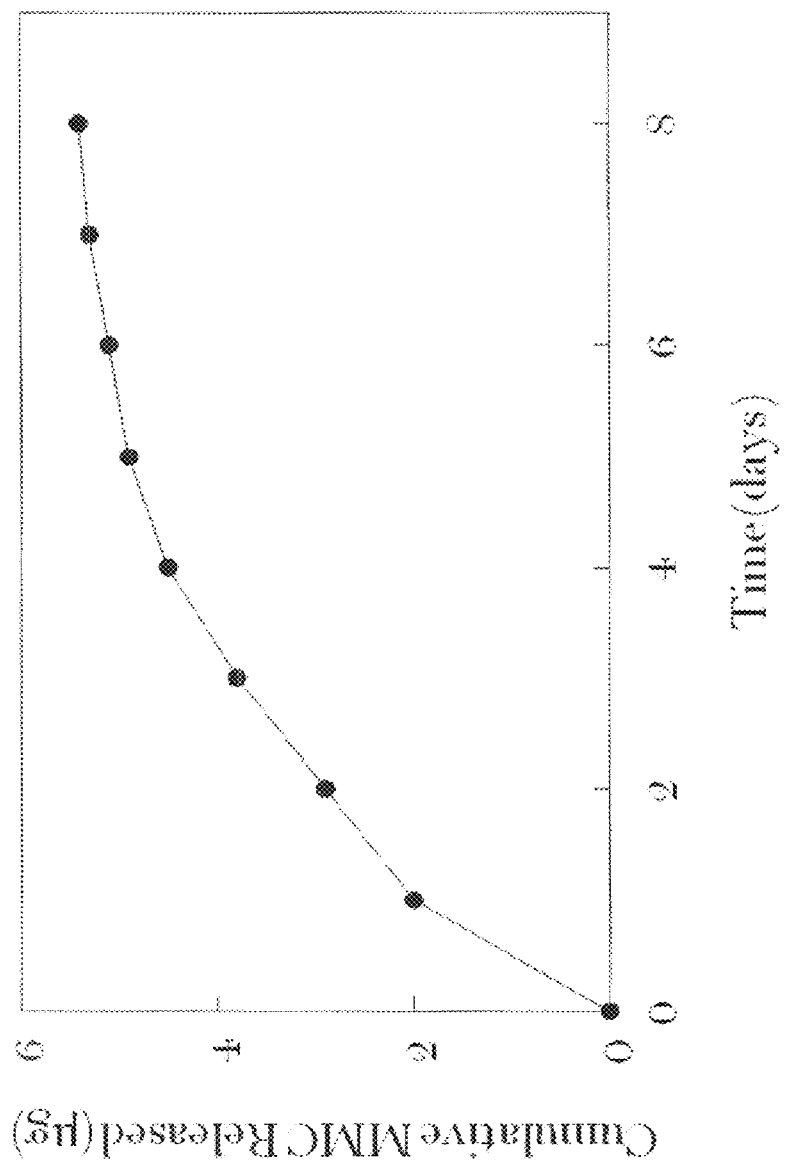
FIG. 15 is a graph depicting the cumulative MMC release profile from p(HEMA) attached to the Ahmed valve. The injection rate used (2.5 µL/min=3.6 ml per day) was similar to the flow of liquid through the Ahmed valve. The released medium was collected daily and analyzed as described below. Water was pumped through the tubing of the valve at the rate equivalent to aqueous circulation. MMC in the effluent was collected over each 24-hour period and quantified by its absorbance at 360 nm. Cumulative MMC release was determined by calculation from individual time points.

The next set of experiments concentrated on the preparation and standardization of p(HEMA) disks loaded with a lower concentration of MMC that could be attached to a commercially available glaucoma drainage device, such as the Ahmed Glaucoma Valve (New World Inc., Rancho Cucamonga, Calif.). Semicircular disks of p(HEMA) (5 mm×6 mm) with incorporated MMC (0.173 mg MMC/g dry gel) were prepared and then attached to the lower half of a commercial Ahmed valve plate (model FP-7), as shown in FIG. 14C, modified for implantation. The arrow shows the p(HEMA) polymer with incorporated MMC. The incorporated MMC imparts the pink color to the polymer. The tube through which aqueous fluid drains is being held by forceps in this photograph FIG. 14C. The release of MMC from this device was measured using a syringe pump to inject sterile water through the tubing of the device. The injection rate was kept constant to emulate aqueous humor circulation in the human eye (2.5 µL aqueous per min or 3.6 mL/day). The MMC released from this device in each 24-hour period was measured and the results are shown in FIG. 15. Water was pumped through the tubing of the valve at the rate equivalent to aqueous circulation. MMC in the effluent was collected over each 24-hour period and quantified by its absorbance at 360 nm. Cumulative MMC release was determined by calculation from individual time points. This device was then implanted into albino New Zealand rabbits. At the end of 3 months the animals were sacrificed and the eyes subjected to histology. The resulting blebs around the plate of the modified Ahmed valve revealed significant reduction in the bleb base-membrane/fibrosis formation, while retaining the surface vascularity. The Ahmed valves removed from the enucleated eyes had released all of their incorporated MMC (as determined by release studies).

Testing of Modified Ahmed Glaucoma Valve

A slow release mitomycin C (p(HEMA)-MMC) device was developed using redox-polymerization techniques discussed above, and a standardized preparation of this drug delivery device as discussed above was attached to an Ahmed Glaucoma Valve (AGV), model FP-7 sold by the New World Medical, Inc. of Rancho Cucamonga, Calif. Semi circular disks of P(HEMA)-MMC (5 mm×6 mm) containing varying concentrations of MMC/g dry weight of the gel were attached to the lower half of an AGV plate. Water was pumped through the modified AGV at a rate comparable to that of aqueous outflow and MMC release was measured. Modified and unmodified AGV were implanted in a rabbit model and drug release and fibrosis were assessed after 3 months. The P(HEMA)-MMC device was found to release MMC over a 1-2 week period in-vitro. Rabbit studies revealed that MMC was released from the disks during the 3-month implantation.

Histological studies demonstrated a significant reduction of inflammatory reaction and fibrosis in the resulting blebs, decreasing the degree of fibrosis and inflammation in the resulting bleb in a rabbit model.

P(HEMA) Sheets

P(HEMA) sheets were prepared as described Experiment 1 by polymerization of 2-hydroxyethymethacylate by redox polymerization in the presence of a cross linker, N,N methylene bis acrylamide in two glass slides with a 0.75 cm spacer. After removing impurities by repetitive swelling in ethanol and water for 12 h each for 2 days, p(HEMA) sheets were cut into semi circular disks measuring 5 mm×6 mm to fit the lower half of the Ahmed glaucoma valve plate (model FP-7). A 1 mm trephine (Ketena Instruments, Fl) was then used to punch a hole in the middle of each disk. The p(HEMA) disks were then loaded with MMC at varying concentrations (0.173 mg, 0.350 mg and 0.8 mg MMC/g dry gel) by a previously described solvent evaporation technique. In this technique, a good solvent, ethanol for MMC and its mixture with water were used for the drug loading experiments.

Previously sterilized FP-7 Ahmed valves were placed in sterile hood. A 1 mm hole was punched into the center of the lower half the end plate. The MMC loaded p(HEMA) disks were then attached to the lower half of the Ahmed glaucoma valve end plate (FP-7) by passing a silicone rivet through the central holes of the two devices. The entire procedure was performed under sterile conditions. The modified GDD was then re-sterilized using UV light under the hood for 5 minutes. UV light was used to prevent degradation of MMC in the p(HEMA) matrix. A total of 24 modified valves were prepared using this technique.

In Vitro Experiments

The purpose of this experiment was to test if the modified Ahmed glaucoma valve would actually release the mitomycin C in a slow and sustained fashion. An in vitro experimental device was constructed using a syringe pump (Harvard Apparatus, model: 55-1144, Freq: 50/60) to inject sterile water through the tubing of the modified Ahmed glaucoma valve. The injection rate was kept constant to emulate aqueous humor circulation in the human eyes (2.5 µL aqueous per min or 3.6 mL/day). The experiment was designed to stimulate the post operative human eye as much as possible. A 30 cc syringe filled with sterile water was attached to the syringe pump. The syringe was attached to one end of a 23 gauge butterfly needle system. The 23 gauge needle itself was then attached to the silicone tube of the modified Ahmed glaucoma valve (FIGS. 14A and 14B). A scintillation vial was used as the collecting media. The modified Ahmed glaucoma valve was then suspended inside the vial and the vial was sealed with parafilm to prevent evaporation. The entire experiment was carried out at room temperature.

At the end of 24 hours, the Ahmed glaucoma valve was removed from the vial and suspended into a new one. The water that was flushed over the p(HEMA) matrix during a 24 hour period was then tested for MMC. This experiment was repeated on a daily basis for one week. The amount of MMC in the collected samples was determined by UV-Vis spectroscopy. MMC has a strong absorption at 360 nm in ethanol. The amount of MMC was calculated from a previously formed calibration curve constructed at 360 nm. Release of MMC was monitored for a total of 7 days.

Results: In Vitro Experiments

FIG. 15 shows the cumulative MMC release results from the in vitro experiments. The initial rate of MMC release was faster than the release rate after 5 days. This is reasonable since the drug molecules that are situated at and around the surface come out first upon contact with water and the drug molecules deeper inside the p(HEMA) gels are released later. After one week, however a light purple color could still be observed in the p(HEMA)-MMC (shown in FIG. 14B), which indicates the presence of residual MMC.

In Vivo Experiments

In vivo experiments were performed on rabbit eyes to test the modified Ahmed valves for 3 reasons:

a. To test the efficacy of the device in terms of release of MMC.

b. To validate the sterilization techniques used.

c. To verify that the concentration of MMC used was sufficient to inhibit fibrosis without collateral damage to the underlying sclera and the surrounding muscles.

All investigations conformed to the regulations of the Association for Research in Vision and Ophthalmology, the National Institutes of Health, and the guidelines set forth by the Tulane IACUC.

Twenty two albino New Zealand rabbits were used in this experiment. In all rabbits, the right eye was used to implant the Ahmed glaucoma valve (AGV). The rabbits were divided into 4 groups. Group A (4 rabbits) received AGVs with no MMC device attached. Group B (6 rabbits) received the modified AGV with 0.173 mg MMC/g dry gel. Group C (6 rabbits) received the modified AGV with 0.350 mg MMC/g dry gel and Group D (6 rabbits) received modified AGV with 0.8 mg MMC/g dry gel.

The surgery was performed in a standard fashion. Following adequate anesthesia using Ketamine, the right eye of the rabbit was prepped with betadine. A 7-0 Vicryl suture was passed through the superior temporal limbus to rotate the eye down. Conjunctival peritomy was then performed at the limbus in the superior temporal quadrant, followed by posterior dissection in the same plane. The dissection was carried between the superior rectus and the lateral rectus muscles posteriorly. The Ahmed glaucoma valve was then brought to the operative site and primed with BSS. The end plate was tucked into the superior temporal quadrant and then secured to the underlying episclera with 2 interrupted 10-0 nylon sutures approximately 7 mm from the limbus. The silicone tube was then cut 0.5 mm anterior to the limbus using a Westcott scissors. A 23-gauge butter fly needle was used to enter the anterior chamber 0.25 mm posterior to the limbus. 0.1 cc of viscoelastic (Healon) was injected into the anterior chamber. The silicone tube was then inserted into the anterior chamber through the needle tract. It was then secured to the surrounding sclera with a 10-0 nylon suture. The conjunctiva was then secured to the limbus with interrupted 10-0 Vicryl suture.

The eye was treated with antibiotic and steroid drops along with cyclogel 1% four times a day for 2 weeks. All animals were examined for signs of infection and tube erosion on days 1, 3, 7, 14 and then monthly. The animals were sacrificed 3 months after implantation. The eyes were then enucleated, taking care not to disturb the bleb and the implant. Following enucleation, 10% formalin was injected into the vitreous cavity to fix the eyes. Twenty four hours later, the eye was dissected with the first incision passing through the middle of the bleb. The Implant end plate was isolated during this process and removed from the eye. The MMC device attached to the end plate of the AGV was then examined. Histology slides were prepared involving the bleb and the surrounding tissues and stained with H &E and Trichrome stains to highlight the basement membrane. The histological sections were examined via light microscopy by a pathologist who was blind to the different groups. Basement membrane measurements were made in micrometers at 20× magnification.

Results: In Vivo Experiments

Figure 16:
FIG. 16 is a photograph of blebs from one of the rabbits following the implantation of a p(HEMA)-MMC-modified Ahmed valve.
Figure 17:
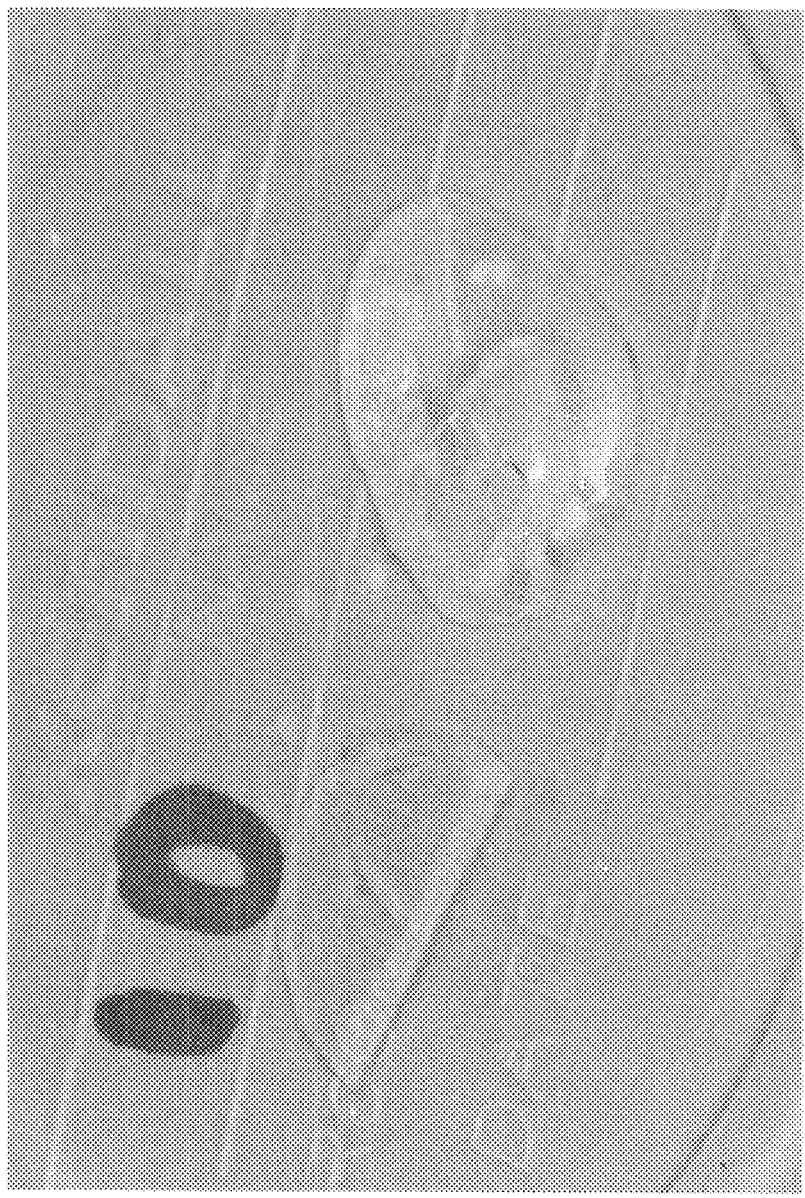
FIG. 17 is a photograph of the modified Ahmed glaucoma valve with the detached P(HEMA)-MMC device. Note the lack of purple color, which indicates that all the MMC has been released into the bleb.

There were no instances of infections, unexpected animal deaths or other complications. All the operations resulted in the formation of a thick-walled vascular bleb (FIG. 16). No avacular cystic blebs were observed even among the MMC groups. After the enucleation, the posterior edge of the bleb was sliced open and the plate of the valve was removed from the bleb with out disturbing the bleb itself. The Ahmed valves were examined with the naked eye. The modified Ahmed valves retained the attached p(HEMA) device. Prior to implantation, the disks were colored purple, indicating the presence of mitomycin C. At the end of the experiments, the disks were colorless, indicating that the mitomycin C had been completely released from the disks (FIG. 17). This was further confirmed by extraction of 3 of the sample disks recovered from the animal experiments No MMC was found by spectroscopic analysis of these ethanol extracts, thus confirming that the disks had released all of the MMC during the 3 month study period.

Histology

Figure 18:
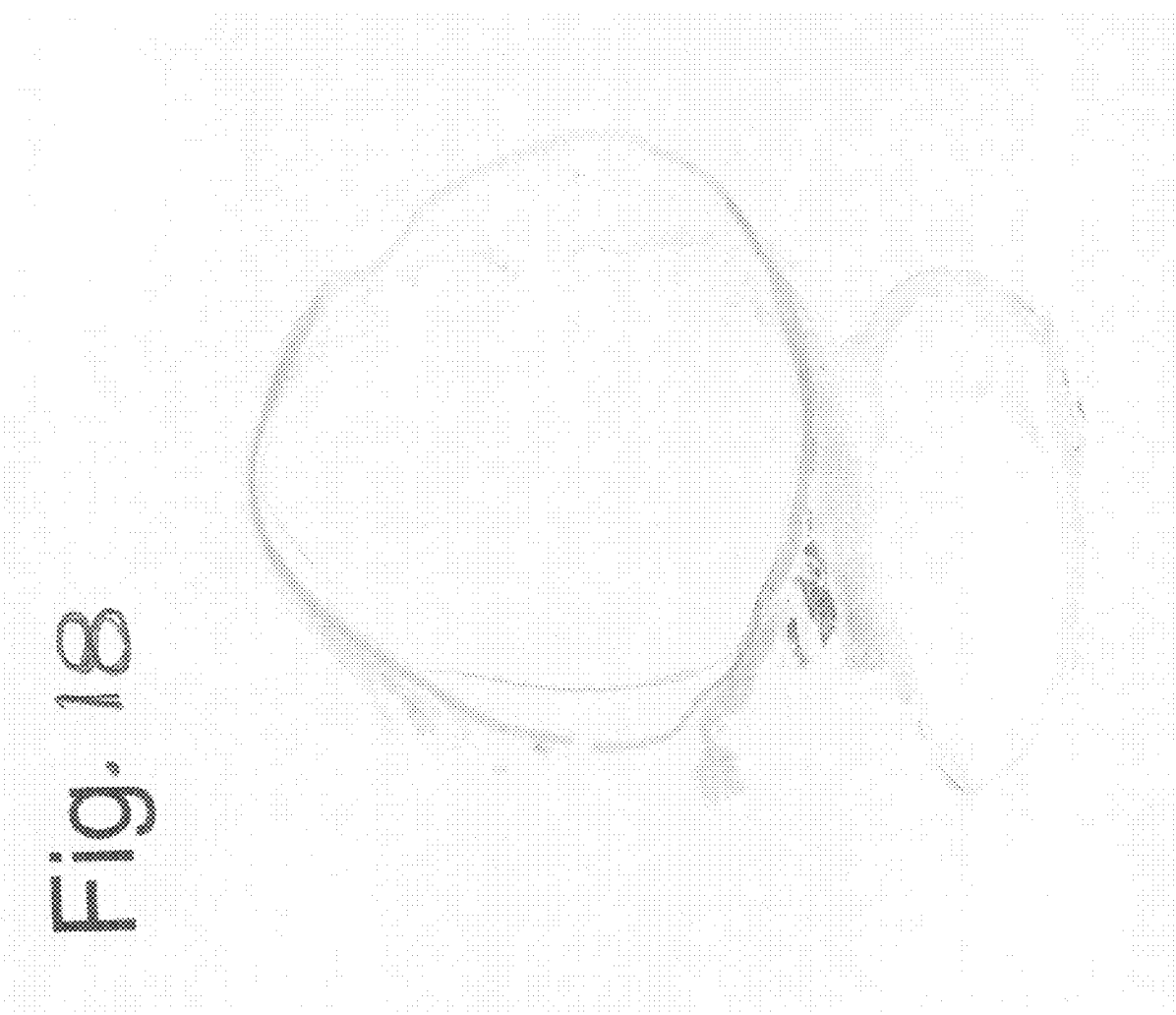
FIG. 18 is a photograph of H and E staining of a bleb following Ahmed glaucoma valve implantation with no mitomycin device attachment. Note that the basement membrane is uniformly thick along the entire bleb.
Figure 19:
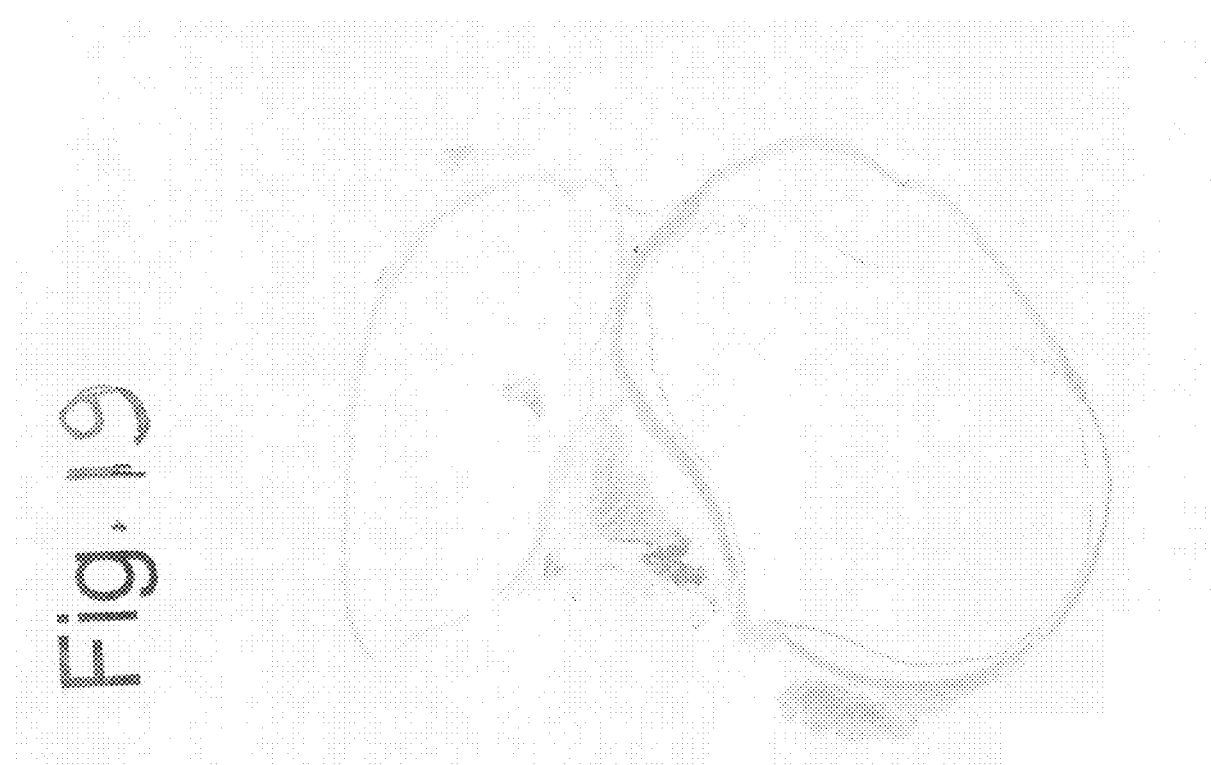
FIG. 19 is a photograph of H and E staining of a bleb following implantation of an Ahmed glaucoma valve modified with MMC-p(HEMA). Note that the basement membrane is thinner in the anterior and posterior edge and the roof of the bleb compared to the floor of the bleb.
Figure 20:
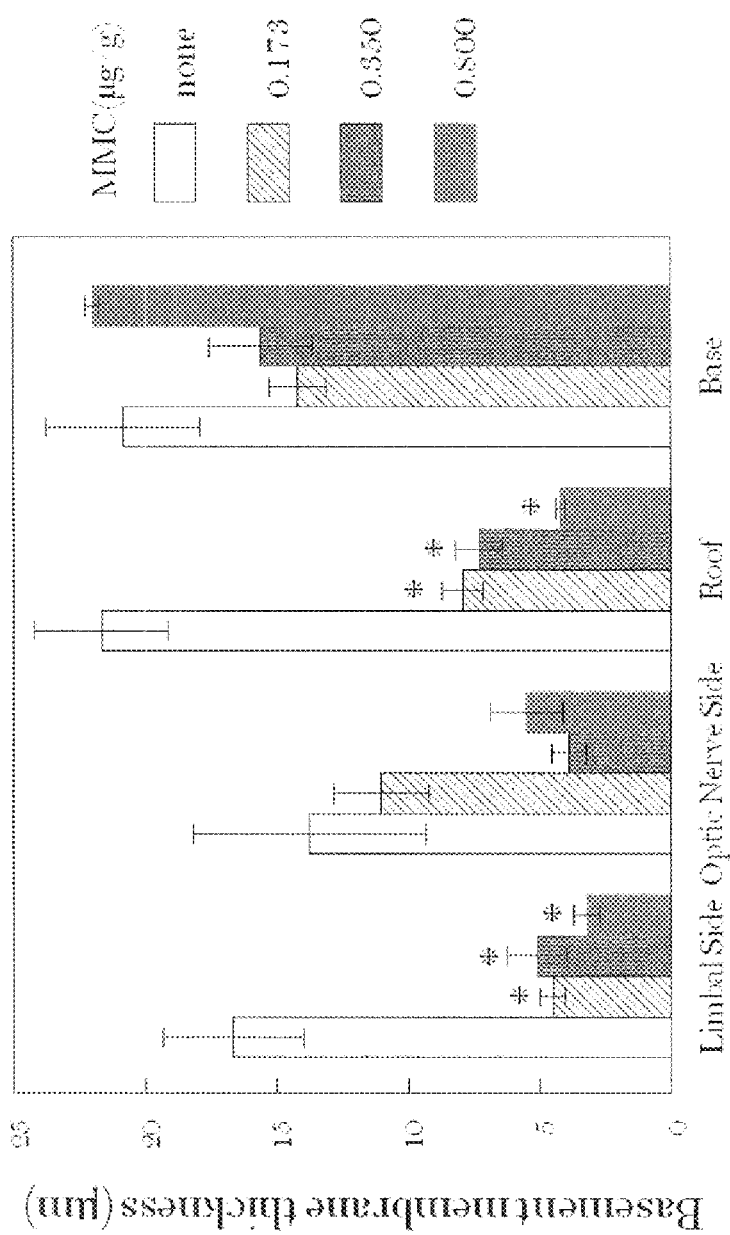
FIG. 20 is a graph depicting the effect of the MMC-p(HEMA)-modified Ahmed glaucoma valve on basement membrane thickness in various regions of the bleb wall. The open bar designated as 'none' represents the control animals implanted with an unmodified Ahmed valve. The shaded bars represent MMC-p(HEMA) modified valves. Data are presented as mean±SEM (n=3, 5 or 6 for various experimental groups). *, $p \leq 0.05$ between this group and the control group.

The basement membrane thickness in various locations and the degree of inflammation was assessed. The basement membrane thickness varied significantly in the roof and the anterior edge of the bleb (the side toward the limbus) when compared to blebs in animals implanted with an unmodified Ahmed valve, as shown in FIGS. 18, 19, and 20. There were no statistically significant differences among the 3 different concentration groups (0.173, 0.35, and 0.8 mg MMC/gram dry weight of p(HEMA)). When these 3 groups were combined in the analysis, the differences between the unmodified and modified Ahmed valves were highly significant. The thickness at the limbal edge of the bleb was reduced from a mean of 16.7 to 4.3 microns ($p=0.00035$) in animals implanted with the MMC-p(HEMA) modified Ahmed valve, while the thickness at the roof of the bleb was reduced from a mean of 21.7 to 6.6 microns ($p=0.000057$), Although there appeared to be a reduction in basement membrane thickness at the posterior edge of the bleb (the side facing the optic nerve, 13.7 versus 7 microns) the means were not statistically different ($p=0.24$). There was no difference in the basement membrane thickness along the floor of the bleb, adjacent to the sclera between the groups (20.8 versus 17.1 microns, $p=0.55$). The degree of inflammation was significantly higher in group A (AGV with out MMC) than the other groups with MMC device.

Discussion of Tests

Trabeculectomy and other peri-limbal surgeries result in the formation of a bleb that acts as a reservoir at the limbus. These blebs are associated with various problems such as bleb leaks, bleb-related infections, and bleb dysesthesia. Post-operative fibrosis leading to the failure of the trabeculectomy operation leads to excessive scar tissue formation in the peri-limbal area making that area less suitable for repeat surgery. These outcomes have led to the increasing use of glaucoma drainage devices (GDD) in the management of patients with glaucoma. GDD surgery results in the formation of the bleb 8-10 mm posterior to the limbus. The presence of the biomaterial of the GDD and the accumulation of the aqueous in the sub-conjunctival space stimulates an inflammatory reaction and fibrosis. This leads to the formation of a well defined bleb surrounding the plate of the GDD. The combination of ongoing inflammation and fibrosis leads to the failure of the operation. From the clinical stand point, the bleb goes through 3 stages: 1. the hypotensive phase, which lasts approximately 1-4 weeks during which phase the intraocular pressure is typically low, the bleb itself is ill defined and diffuse and exhibits congested blood vessels. 2. The hypertensive phase, which lasts from 1-6 months and is associated with elevated intraocular pressure. The bleb becomes localized and well defined with a formation of a dense fibrous capsule separating the aqueous from the conjunctival blood vessels. 3. The stable phase, which is achieved at the end of six months and is characterized by the presence of a bleb with no or little inflammation and well controlled intraocular pressures, usually in the mid-teens. The incidence of the hypertensive phase has been reported to be between 10-50% and varies with the different GDDs. Generally, it is accepted that the incidence is lower with the Baerveldt implant compared to the Ahmed glaucoma valve. During this phase, the IOP can potentially increase to 30-50 mm Hg. The overall failure rate of the GDDs is approximately 10% every year, leading to 50% failure rate at the end of 5 years. This is the result of continued fibrosis. One time application of anti-fibrosis drugs such as mitomycin-C or 5-Fluoro-uracil at the time of the operation, has not been effective reducing fibrosis in these GDD surgeries[1], unlike that noticed following trabeculectomy. In the TVT study comparing the Baerveldt implant vs trabeculectomy in patients with previously failed trabeculectomy operation, the GDD group was found more likely to maintain IOP control, avoid persistent hypotony or reoperation for glaucoma and had less incidence of postoperative complications than trabeculectomy with MMC during the first year of follow-up. A recent paper suggested increased success with lower incidence of hypertensive phase in patients receiving repeated injections of 5-fluorouracil into the bleb following the application of MMC at the time of surgery in patients with Ahmed glaucoma valve implantation. Thus, the GDD surgery has several advantages over the traditional trabeculectomy operation. However, the inflammatory reaction that results in the hypertensive phase and the continued fibrosis leading to complete failure are the main problems that need to be overcome to make the surgery better. The creation of a slow release MMC drug coated GDD is an attempt to overcome these problems.

The drug delivery system was verified both in vitro (laboratory) and in vivo (cell culture and rabbit) models. The effect of the MMC on the bleb reflects the pattern of release of mitomycin C upon contact with the aqueous. In the presence of aqueous, the p(HEMA) polymer swells releasing the mitomycin C into the aqueous. Since the plate of the AGV prevents contact of the aqueous for the most part from the sclera, most of the effect of the drug should be found on the roof and the anterior side wall of the bleb. The histology results demonstrated this to be true. In the groups with MMC, the thickness of the basement membrane was significantly thinner in the roof and the anterior edge of the bleb compared to the group with no MMC. However, there were no differences among the groups with 3 different concentrations of MMC. It may be that the degree of anti-inflammatory and anti-fibrotic action of MMC was similar in the range of concentrations that were used in these experiments.

CONCLUSIONS

The in vivo and in vitro experiments proved that mitomycin C was released in a sustained release fashion from the p(HEMA) disks following their attachment to the Ahmed glaucoma valve. The fact that MMC was recovered following the UV sterilization demonstrates that the technique of sterilization that used in these experiments were successful, both in ensuring sterility while not damaging the drug. The concentration of MMC in the p(HEMA) was high enough to prevent significant fibrosis in the bleb while avoiding the formation of avascular blebs.

SCOPE OF THE INVENTION

The above presents a description of the best mode contemplated of carrying out my invention, and of the manner and process of making and using it, in such full, clear, concise, and exact terms as to enable any person skilled in the art to which it pertains to make and use my invention. My invention is, however, susceptible to modifications and alternate constructions from the illustrative embodiments discussed above which are fully equivalent. Consequently, it is not the intention to limit my invention to the particular embodiments disclosed. On the contrary, my intention is to cover all modifications and alternate constructions coming within the spirit and scope of my invention as generally expressed by the following claims, which particularly point out and distinctly claim the subject matter of my invention:

The invention claimed is:

1. An implantable glaucoma drainage device including
a tube extending from the device that has a terminal end adapted to be placed within an intraocular chamber of an eye, and
a plate having on a surface of the plate, as a separate element, a porous polymeric member comprising P-HEMA hydrogel, said member carrying an antifibrotic agent,
said device configured to be implantable within a surgical incision in a surface of an eye and a sufficient amount of the antifibrotic agent being retained by the porous polymeric member so that, upon implantation of the device, the antifibrotic agent on contact by an aqueous medium from the eye is released into the incision slowly over a prolonged period in excess of 1 week.

2. The glaucoma drainage device of claim 1 where the antifibrotic agent is released at a rate of substantially from 0.03 to 0.09 milligrams per hour.

3. The glaucoma drainage device of claim 2 where the antifibrotic agent is 5-flurouracil.

4. The glaucoma drainage device of claim 2 where the antifibrotic agent is mitomycin-C.

5. The glaucoma drainage device of claim 1 where the P-HEMA hydrogel is made by redox polymerization with impurities removed.

6. The glaucoma drainage device of claim 1 where the porous polymeric member is a disk.

7. The glaucoma drainage device of claim 1 where the porous polymeric member is a sheet.

8. An implantable glaucoma drainage device including
a tube extending from the device that has a terminal end adapted to be placed within an intraocular chamber of an eye, and
a plate having on a surface of the plate, as a separate element, a porous, biodegradable, polymeric member comprising polylactides and glycolic acid copolymers, said member carrying an antifibrotic agent,
said device configured to be implantable within a surgical incision in a surface of an eye and a sufficient amount of the antifibrotic agent being retained by the porous polymeric member so that, upon implantation of the device, the antifibrotic agent on contact by an aqueous medium from the eye is released into the incision slowly over a prolonged period in excess of 1 week.

9. The glaucoma drainage device of claim 8 where the antifibrotic agent is released at a rate of substantially from 0.03 to 0.09 milligrams per hour.

10. The glaucoma drainage device of claim 9 where the antifibrotic agent is 5-flurouracil.

11. The glaucoma drainage device of claim 9 where the antifibrotic agent is mitomycin-C.

12. The glaucoma drainage device of claim 8 where the porous polymeric member is a disk.

13. The glaucoma drainage device of claim 8 where the porous polymeric member is a sheet.

14. An implantable glaucoma drainage device including
a plate for collecting an aqueous medium from an intraocular chamber of an eye,
a tube extending from the device that has a terminal end adapted to be placed within an intraocular chamber of an eye, said aqueous medium flowing at least in part through the tube to the plate,
said plate having a surface to which is attached, as a separate element, a porous polymeric member carrying an antifibrotic agent, said polymeric member positioned on the plate to receive the aqueous medium so that said aqueous medium contacts and the flows over or through the polymeric member to wash the antifibrotic agent from the polymeric member and into the surgical incision,
said device configured to be implantable within a surgical incision in a surface of an eye and a sufficient amount of the antifibrotic agent being retained by the porous polymeric member so that, upon implantation of the device, the antifibrotic agent on contact by the aqueous medium is released into the incision slowly over a prolonged period in excess of 1 week.

15. The glaucoma drainage device of claim 14 where said polymeric member has width substantially from 4 mm to 15 mm, a length substantially from 4 mm to 15 mm, and a thickness substantially from 0.25 mm to 1.00 mm.

16. The glaucoma drainage device of claim 15 where the antifibrotic agent is released at a rate of substantially from 0.03 to 0.09 milligrams per hour.

17. The glaucoma drainage device of claim 16 where the antifibrotic agent is 5-flurouracil.

18. The glaucoma drainage device of claim 16 where the antifibrotic agent is mitomycin-C.

19. The glaucoma drainage device of claim 14 porous, biodegradable, polymeric member comprising polylactides and glycolic acid copolymers.

20. The glaucoma drainage device of claim 14 where the porous polymeric member is a disk.

21. The glaucoma drainage device of claim 14 where the porous polymeric member is a sheet.

22. An implantable glaucoma drainage device including
a plate for collecting an aqueous medium from an intraocular chamber of an eye,
a tube extending from the device that has a terminal end adapted to be placed within an intraocular chamber of an eye, said aqueous medium flowing at least in part through the tube to the plate,
said plate having a surface to which is attached a porous polymeric member carrying an antifibrotic agent, said polymeric member positioned on the plate to receive the aqueous medium so that said aqueous medium contacts and the flows over or through the polymeric member to wash the antifibrotic agent from the polymeric member and into the surgical incision,
said device configured to be implantable within a surgical incision in a surface of an eye and a sufficient amount of the antifibrotic agent being retained by the porous polymeric member so that, upon implantation of the device, the antifibrotic agent on contact by the aqueous medium is released into the incision slowly over a prolonged period in excess of 1 week, where the porous polymeric member comprises P-HEMA hydrogel and a silicone rivet attaches the polymeric member to the plate.

23. A method of treating glaucoma comprising (a) implanting a device into a surgical incision in a surface of an eye under the eye's conjunctival/Tenons' pocket approximately 7-10 millimeters from the eye's limbus, said device including a tube extending from the device that has a terminal end adapted to be placed within an intraocular chamber of an eye, and a plate having on a surface of the plate, as a separate element, a porous polymeric member comprising P-HEMA hydrogel, said member carrying an antifibrotic agent, said device configured to be implantable within a surgical incision in a surface of an eye and a sufficient amount of the antifibrotic agent being retained by the porous polymeric member so that, upon implantation of the device, the antifibrotic agent on contact by an aqueous medium from the eye is released into the incision slowly over a prolonged period in excess of 1 week, (b) suturing in position, (c) inserting the tube terminal end into an intraocular chamber the eye.

24. A method of treating glaucoma comprising (a) implanting a device into a surgical incision in a surface of an eye under the eye's conjunctival/Tenons' pocket approximately 7-10 millimeters from the eye's limbus, said device including a tube extending from the device that has a terminal end adapted to be placed within an intraocular chamber of an eye, and a plate having on a surface of the plate, as a separate element, a porous, biodegradable, polymeric member comprising polylactides and glycolic acid copolymers, said member carrying an antifibrotic agent, said device configured to be implantable within a surgical incision in a surface of an eye and a sufficient amount of the antifibrotic agent being retained by the porous polymeric member so that, upon implantation of the device, the antifibrotic agent on contact by an aqueous medium from the eye is released into the incision slowly over a prolonged period in excess of 1 week, (b) suturing in position, (c) inserting the tube terminal end into an intraocular chamber the eye.

25. A method of treating glaucoma comprising (a) implanting a device into a surgical incision in a surface of an eye under the eye's conjunctival/Tenons' pocket approximately 7-10 millimeters from the eye's limbus, said device including a plate for collecting an aqueous medium from an intraocular chamber of an eye, a tube extending from the device that has a terminal end adapted to be placed within an intraocular chamber of an eye, said aqueous medium flowing at least in part through the tube to the plate, said plate having a surface to which is attached, as a separate element, a porous polymeric member carrying an antifibrotic agent, said polymeric member positioned on the plate to receive the aqueous medium so that said aqueous medium contacts and the flows over or through the polymeric member to wash the antifibrotic agent from the polymeric member and into the surgical incision, said device configured to be implantable within a surgical incision in a surface of an eye and a sufficient amount of the antifibrotic agent being retained by the porous polymeric member so that, upon implantation of the device, the antifibrotic agent on contact by the aqueous medium is released into the incision slowly over a prolonged period in excess of 1 week, (b) suturing in position, (c) inserting the tube terminal end into an intraocular chamber the eye.

* * * * *